(12) United States Patent
Subramanian et al.

(10) Patent No.: US 11,147,671 B2
(45) Date of Patent: Oct. 19, 2021

(54) METHODS, IMPLANTS, AND SYSTEMS FOR TREATMENT OF MITRAL VALVE PROLAPSE

(71) Applicant: CREATIVE HEART VALVE SOLUTIONS LLC, New York, NY (US)

(72) Inventors: Valavanur A. Subramanian, New York, NY (US); Nirav C. Patel, New York, NY (US)

(73) Assignee: CREATIVE HEART VALVE SOLUTIONS LLC, New York, NY (US)

( * ) Notice: Subject to any disclaimer, the term of this patent is extended or adjusted under 35 U.S.C. 154(b) by 0 days.

(21) Appl. No.: 17/136,855

(22) Filed: Dec. 29, 2020

(65) Prior Publication Data

US 2021/0196463 A1     Jul. 1, 2021

Related U.S. Application Data

(60) Provisional application No. 62/955,976, filed on Dec. 31, 2019.

(51) Int. Cl.
*A61F 2/24*     (2006.01)

(52) U.S. Cl.
CPC .......... *A61F 2/2463* (2013.01); *A61F 2/2466* (2013.01); *A61F 2220/0075* (2013.01)

(58) Field of Classification Search
CPC .... A61F 2/2463; A61F 2/2439; A61F 2/2466; A61F 2/2442; A61F 2/2454; A61F 2/2457; A61F 2/246; A61F 2/222; A61F 2/0075; A61F 2220/0008; A61F 2220/0016; A61F 2250/0007; A61F 2250/0008; A61F 2250/0064; A61F 2250/0065

See application file for complete search history.

(56) References Cited

U.S. PATENT DOCUMENTS

| | | | |
|---|---|---|---|
| 2005/0070999 A1* | 3/2005 | Spence | A61F 2/2454 623/2.37 |
| 2013/0211513 A1* | 8/2013 | Rourke | A61F 2/2442 623/2.37 |
| 2015/0313620 A1 | 11/2015 | Suri | |
| 2015/0366666 A1 | 12/2015 | Khairkhahan et al. | |
| 2016/0278921 A1* | 9/2016 | Longoria | A61B 17/06166 |

(Continued)

FOREIGN PATENT DOCUMENTS

| WO | WO 2004/103162 | 12/2004 |
|---|---|---|
| WO | WO 2019/222694 | 11/2019 |

OTHER PUBLICATIONS

International Search Report and Written Opinion for Application No. PCT/US2020/067333 dated Apr. 22, 2021; 12 pages.

*Primary Examiner* — Paul B Prebilic
(74) *Attorney, Agent, or Firm* — Knobbe, Martens, Olson & Bear, LLP

(57) ABSTRACT

Disclosed herein are methods, implants and systems for treatment of mitral valve prolapse by subannular fixation of the prolapsed mitral valve. The disclosure relates generally to the field of heart valve repair devices, methods and kits and more specifically to trans catheter methods and devices for insertion of tethers and anchors to the mitral valve leaflets for reduction the prolapsed mitral valve and subannular fixation of the prolapsed leaflet to treat mitral valve regurgitation.

19 Claims, 28 Drawing Sheets

(56) References Cited

U.S. PATENT DOCUMENTS

| | | | |
|---|---|---|---|
| 2018/0185152 A1* | 7/2018 | Bishop | A61B 17/0401 |
| 2018/0214270 A1* | 8/2018 | Subramanian | A61F 2/2457 |
| 2019/0076247 A1 | 3/2019 | Zeng | |
| 2019/0167429 A1* | 6/2019 | Stearns | A61F 2/2442 |

* cited by examiner

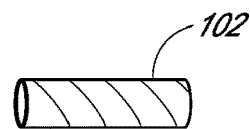
FIG. 16A
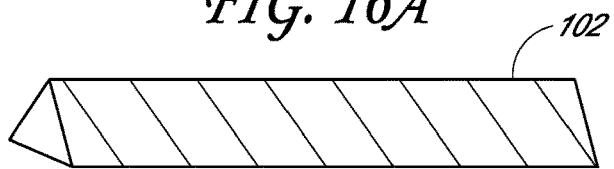
FIG. 16B
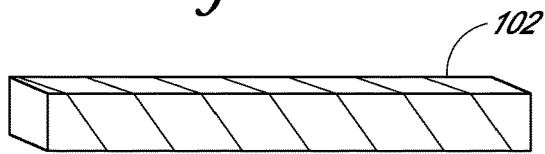
FIG. 16C
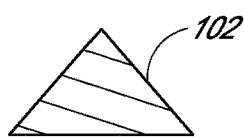 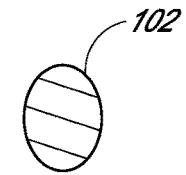 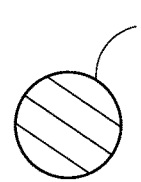
FIG. 16D  FIG. 16E  FIG. 16F
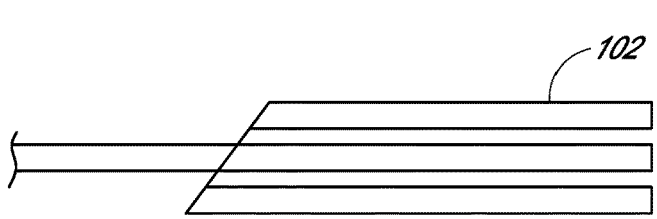 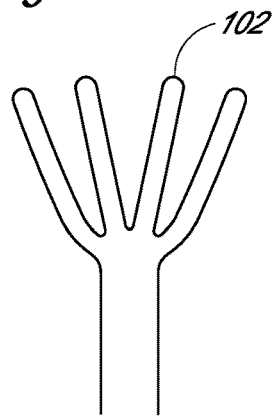
FIG. 16G
FIG. 16H
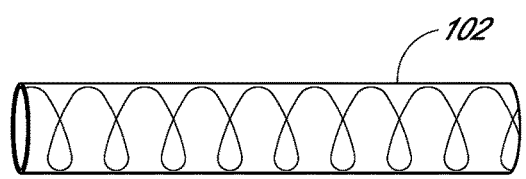
FIG. 16I
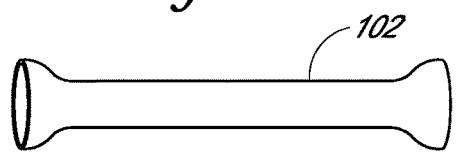 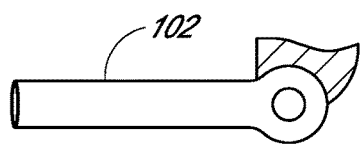
FIG. 16J  FIG. 16K

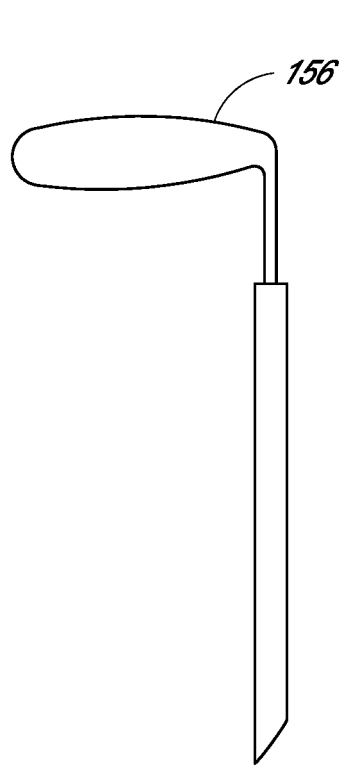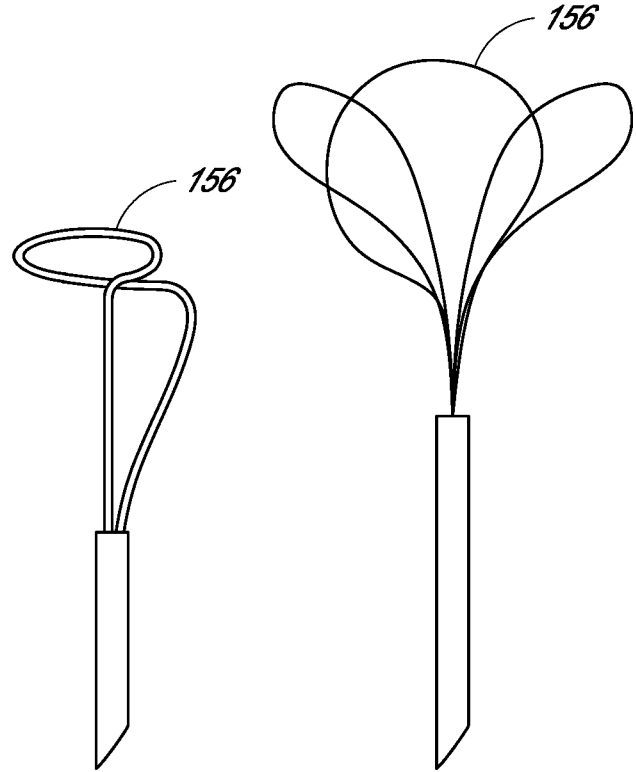
FIG. 23A     FIG. 23B     FIG. 23C

METHODS, IMPLANTS, AND SYSTEMS FOR TREATMENT OF MITRAL VALVE PROLAPSE

CROSS-REFERENCE TO RELATED APPLICATIONS

This application claims priority benefit to U.S. Provisional Patent Application No. 62/955,976, filed Dec. 31, 2019, the entirety of which is hereby incorporated by reference herein.

BACKGROUND

Field of the Invention

Some embodiments relate generally to methods, implants, and systems for treatment of mitral valve prolapse. Some embodiments relate to treatment by sub-annular fixation of the prolapsed mitral valve leaflet.

Description of the Related Art

The mitral valve includes an anterior leaflet and a posterior leaflet. The leaflets are fixed to an annulus. The subvalvular combination of chordae and papillary muscles normally prevents the mitral valve from prolapsing into the left atrium. In a malfunctioning mitral valve, there can be increased leaflet movement such as leaflet prolapse and/or decreased leaflet movement such as restricted leaflet motion such as an obstruction. In leaflet prolapse, a portion of the leaflet extends beyond the plane of the annulus during ventricular contraction.

Notwithstanding the presence of presently available methods, implants, and systems, there remains a need for a simple but effective methods, implants, and systems to reduce mitral valve prolapse.

SUMMARY

In some embodiments, an objective is to restore normal function of the mitral valve. This can be accomplished by restructuring the valve and/or a portion of the valve, such as a leaflet, to prevent or reduce valvular insufficiency, including but not limited to valve prolapse.

In some embodiments, a system can include any number of features disclosed herein.

In some embodiments, a method can include any number of features disclosed herein.

In some configurations, disclosed herein is a method of treating a mitral valve, comprising accessing a native valve leaflet; anchoring an implant in the subannular space; and coupling the implant to the native valve leaflet. In some embodiments, the method does not involve any attachment to the papillary muscles or chordae tendinae.

In some configurations, the implant is anchored within about 3 cm, 2 cm, 1 cm, or less from the mitral valve annulus.

Also disclosed herein is a method of subannular anchoring, comprising: positioning a leaflet anchor implant adjacent to a prolapsed leaflet; positioning a subannular implant between the prolapsed leaflet and the annulus, in the subannular space; tensioning a tether coupled to the leaflet anchor implant; and securing the tether.

In some configurations, the tether extends through the subannular implant.

In some configurations, securing the tether comprises securing the tether to the annulus.

In some configurations, the method further comprises selecting the subannular implant from a plurality of subannular implants having different shapes.

In some configurations, the method further comprises selecting the subannular implant from a plurality of subannular implants having different flexibilities.

In some configurations, the method further comprises selecting the subannular implant from a plurality of subannular implants having different lengths.

In some configurations, the subannular implant is positioned and/or anchored entirely below the surface, e.g., inferior surface of the annulus.

In some configurations, the subannular implant extends in an arc between the annulus and the prolapsed leaflet.

In some configurations, the leaflet anchor implant is entirely in the mitral valve orifice.

In some configurations, a lock that secures the tether is entirely in the left atrium.

In some embodiments, disclosed herein is a subannular anchoring implant, that can comprise one or more of: a leaflet anchor implant configured to be positioned on a first side of a prolapsed leaflet; a subannular implant configured to be positioned on a second side of the prolapsed leaflet, the first side opposite the second side; a tether; and/or a lock.

In some configurations, the tether is configured to be tightened to reduce prolapse.

In some configurations, the tether is configured to be secured by the lock after being tightened.

In some configurations, the subannular implant is configured to span a subannular distance between the annulus and the prolapsed leaflet.

In some configurations, the subannular implant is configured to span a subannular arc between the annulus and the prolapsed leaflet.

In some configurations, the subannular implant is flexible.

In some configurations, the subannular implant is rigid.

In some configurations, the subannular implant is hollow to accept the tether therethrough.

In some configurations, the leaflet anchor implant is configured to be delivered through a hole formed in the prolapsed leaflet.

In some configurations, the leaflet anchor implant is configured to be delivered in a compressed configuration.

In some configurations, the leaflet anchor implant is configured to be delivered to the mitral valve orifice.

In some configurations, the system further comprises a steerable stabilizing template catheter configured to be positioned on the annulus.

In some configurations, the system further comprises a piercing needle configured to pass through the steerable stabilizing template catheter to penetrate the annulus.

In some configurations, the system further comprises a leaflet capturing element configured to pass through the annulus and configured to capture the prolapsed leaflet.

In some configurations, the system further comprises a piercing needle configured to pass through the leaflet capturing element to penetrate the leaflet and deliver the leaflet anchor implant.

In some configurations, the tether is coupled to the leaflet anchor implant.

In some configurations, the leaflet anchor implant comprises a mattress suture.

In some configurations, the leaflet anchor implant comprises one or more knots.

In some configurations, the system further comprises a leaflet capturing element comprising a pair of grasping arms.

In some configurations, the leaflet anchor implant comprises a pair of discs comprising one or more interdigitating members carried by the leaflet capturing element.

In some configurations, the leaflet anchor implant comprises a pair of discs comprising one or more interdigitating members.

In some configurations, the lock comprises a lock positioned on the annulus and a lock positioned in the subannular space.

In some configurations, the subannular implant comprises a spring.

In some configurations, the subannular implant comprises a flared tube.

In some configurations, the subannular implant comprises a rotatable cam drive.

In some configurations, the subannular implant is configured to be positioned in a plurality of rotational positions.

In some configurations, the system further comprises a guiding catheter configured to be moved through the mitral orifice from the left atrium to the left ventricle.

In some configurations, the system further comprises a piercing needle configured to pass through the guiding catheter to penetrate the annulus from the subannular space.

In some configurations, the system further comprises a basket catheter configured to capture a centigrade guide wire.

In some configurations, the basket catheter comprises one or more loops.

In some configurations, the system further comprises a piercing needle passed from below the mitral annulus into the left atrium.

In some configurations, the system further comprises a basket catheter configured to capture a guide wire passed through the piercing needle, the basket catheter configured to be passed from a trans-septal guiding catheter in an antegrade access via the femoral vein.

In some configurations, the system further comprises a secondary lock and a secondary tether configured to be positioned on the other leaflet.

In some configurations, the tether and the secondary tether are configured to be tightened.

In some configurations, the system further comprises a crimping stabilizing element configured to couple to the tether and the secondary tether.

In some configurations, the system further comprises a secondary leaflet anchor implant configured to be positioned on a first side of the other leaflet; a secondary subannular implant configured to be positioned on a second side of the other leaflet, the first side opposite the second side; a secondary tether; and a secondary lock.

In some embodiments, a method of treating a mitral valve is provided. The method can include accessing a native valve leaflet. The method can include anchoring an implant in the subannular space. The method can include coupling the implant to the native valve leaflet. In some embodiments, the method does not involve any attachment to the papillary muscles or chordae tendinae.

In some embodiments, the implant is anchored within about 2 cm from the mitral valve annulus. In some embodiments, the implant is anchored within about 1 cm from the mitral valve annulus.

In some embodiments, a method of subannular anchoring is provided. The method can include positioning a leaflet anchor implant adjacent to a prolapsed leaflet. The method can include positioning a subannular implant between the prolapsed leaflet and the annulus, in the subannular space. The method can include tensioning a tether coupled to the leaflet anchor implant. The method can include securing the tether.

In some embodiments, the tether extends through the subannular implant. In some embodiments, securing the tether comprises securing the tether to the annulus. In some embodiments, the method can include selecting the subannular implant from a plurality of subannular implants having different shapes. In some embodiments, the method can include selecting the subannular implant from a plurality of subannular implants having different flexibilities. In some embodiments, the method can include selecting the subannular implant from a plurality of subannular implants having different lengths. In some embodiments, the subannular implant is entirely below the surface of the annulus. In some embodiments, the subannular implant extends in an arc between the annulus and the prolapsed leaflet. In some embodiments, the leaflet anchor implant is entirely in the mitral valve orifice. In some embodiments, a lock that secures the tether is entirely in the left atrium.

In some embodiments, a subannular anchoring system is provided. The subannular anchoring system can include a leaflet anchor implant configured to be positioned on a first side of a prolapsed leaflet. The subannular anchoring system can include a subannular implant configured to be positioned on a second side of the prolapsed leaflet, the first side opposite the second side. The subannular anchoring system can include a tether. The subannular anchoring system can include a lock.

In some embodiments, the tether is configured to be tightened to reduce prolapse. In some embodiments, the tether is configured to be secured by the lock after being tightened. In some embodiments, the subannular implant is configured to span a subannular distance between the annulus and the prolapsed leaflet. In some embodiments, the subannular implant is configured to span a subannular arc between the annulus and the prolapsed leaflet. In some embodiments, the subannular implant is flexible. In some embodiments, the subannular implant is rigid. In some embodiments, the subannular implant is hollow to accept the tether therethrough. In some embodiments, the leaflet anchor implant is configured to be delivered through a hole formed in the prolapsed leaflet. In some embodiments, the leaflet anchor implant is configured to be delivered in a compressed configuration. In some embodiments, the leaflet anchor implant is configured to be delivered to the mitral valve orifice. In some embodiments, the subannular anchoring system can include a steerable stabilizing template catheter configured to be positioned on the annulus. In some embodiments, the subannular anchoring system can include a piercing needle configured to pass through the steerable stabilizing template catheter to penetrate the annulus. In some embodiments, the subannular anchoring system can include a leaflet capturing element configured to pass through the annulus and configured to capture the prolapsed leaflet. In some embodiments, the subannular anchoring system can include a piercing needle configured to pass through the leaflet capturing element to penetrate the leaflet and deliver the leaflet anchor implant. In some embodiments, the tether is coupled to the leaflet anchor implant. In some embodiments, the leaflet anchor implant comprises a mattress suture. In some embodiments, the leaflet anchor implant comprises one or more knots. In some embodiments, the subannular anchoring system can include a leaflet capturing element comprising a pair of grasping arms. In some embodiments, the leaflet anchor implant comprises a pair of discs comprising one or more interdigitating members carried by the leaflet capturing element. In some embodiments, the leaflet anchor implant comprises a pair of discs comprising one or more interdigitating members. In some embodiments, the lock comprises a lock positioned on the annulus and a lock positioned in the subannular space. In some embodiments, the subannular implant comprises a spring. In some embodiments, the subannular implant comprises a flared tube. In some embodiments, the subannular implant comprises a rotatable cam drive. In some embodiments, the subannular implant is configured to be positioned in a plurality of rotational positions. In some embodiments, the subannular anchoring system can include a guiding catheter configured to be moved through the mitral orifice from the left atrium to the left ventricle. In some embodiments, the subannular anchoring system can include a piercing needle configured to pass through the guiding catheter to penetrate the annulus from the subannular space. In some embodiments, the subannular anchoring system can include a basket catheter configured to capture a centigrade guide wire. In some embodiments, the basket catheter comprises one or more loops. In some embodiments, the subannular anchoring system can include a piercing needle passed from below the mitral annulus into the left atrium. In some embodiments, the subannular anchoring system can include a basket catheter configured to capture a guide wire passed through the piercing needle, the basket catheter configured to be passed from a trans-septal guiding catheter in an antegrade access via the femoral vein. In some embodiments, the subannular anchoring system can include a secondary lock and a secondary tether configured to be positioned on the other leaflet. In some embodiments, the tether and the secondary tether are configured to be tightened. In some embodiments, the subannular anchoring system can include a crimping stabilizing element configured to couple to the tether and the secondary tether. In some embodiments, the subannular anchoring system can include a secondary leaflet anchor implant configured to be positioned on a first side of the other leaflet; a secondary subannular implant configured to be positioned on a second side of the other leaflet, the first side opposite the second side; a secondary tether; and a secondary lock.

BRIEF DESCRIPTION OF THE DRAWINGS

FIGS. 16A-16K shows embodiments of the subannular implant.

FIGS. 23A-23C shows embodiments of a basket catheter.

DETAILED DESCRIPTION

Figure 1:
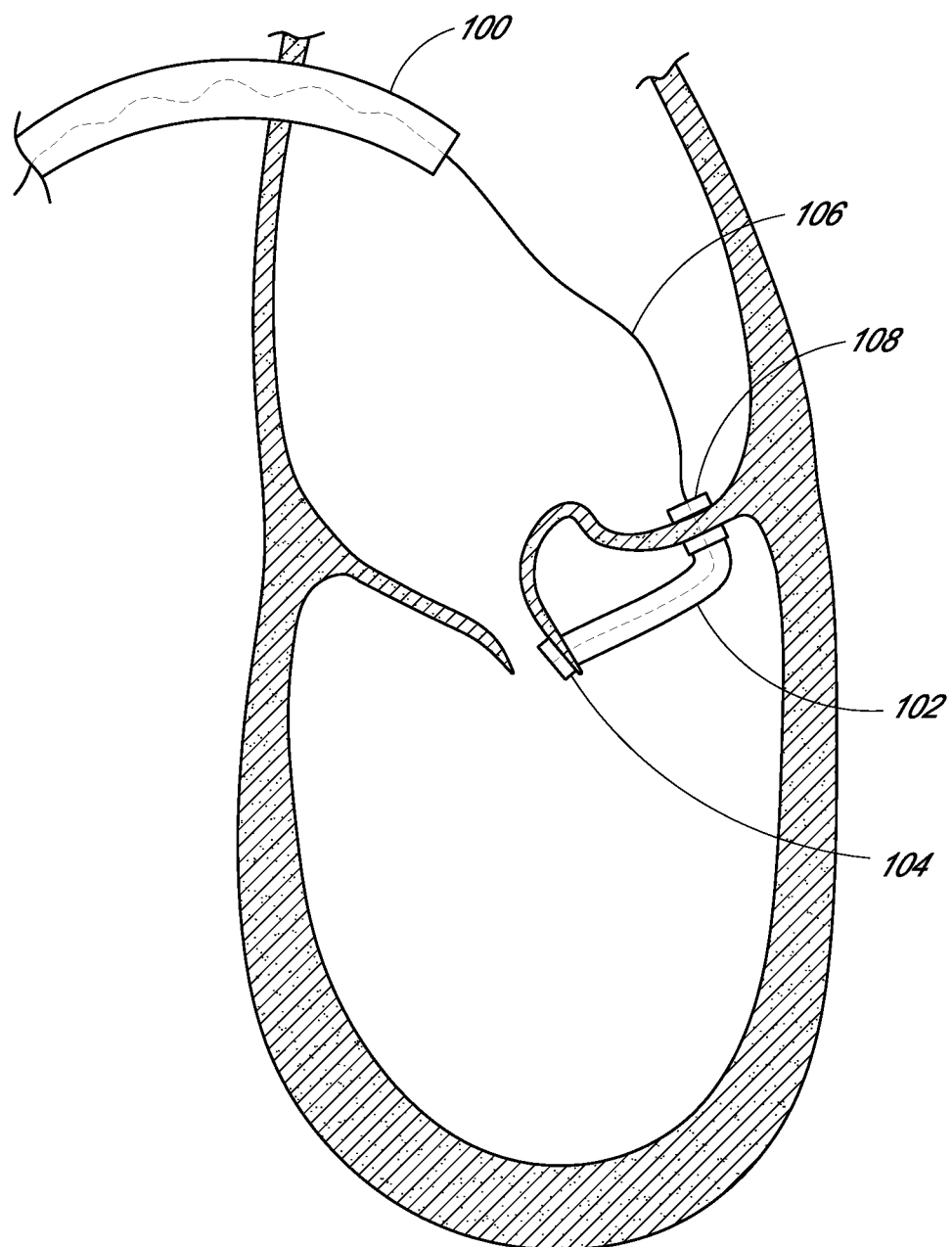
FIG. 1 shows an embodiment of a guiding catheter in a left atrium.

The disclosure relates in some aspects to methods, implants, and systems for treatment of mitral valve prolapse. The disclosure relates in some aspects to transcatheter techniques. The disclosure also relates in some aspects to subannular fixation of the prolapsed mitral valve.

In some embodiments, a guiding catheter is advanced percutaneously from a femoral vein, into the right atrium, through the fossa ovalis. The guiding catheter can be advanced into the left atrium. In some embodiments, a steering catheter is advanced through the guiding catheter. The steering catheter can include an annular piercing element. In some embodiments, while generally described as a subannular implant configured for reducing or preventing mitral valve prolapse or other valvular conditions, an implant can be positioned subannularly or alternatively at other desired anatomic locations within, for example, the heart. The steering catheter can carry the subannular implant. In some embodiments, a leaflet anchor implant is provided. The steering catheter can carry the leaflet anchor implant. The steering catheter can position the subannular implant and the leaflet anchor implant as described herein. In other embodiments, transapical or open surgical techniques can be utilized.

The steering catheter can be advanced from the atrial side of the mitral annulus into the subannular space. The subannular implant and the leaflet anchor implant can be steered into position by the steering catheter. The steering catheter can position the subannular implant in the subannular space. The steering catheter can position the leaflet anchor implant adjacent to the prolapsed leaflet within the mitral valve orifice.

The subannular implant can be positioned in and/or anchored to tissue in a space below the annulus, from immediately adjacent to the annulus to a distance below the annulus, for example, at, or within no more than about 5 mm below the annulus, 10 mm below the annulus, 15 mm below the annulus, 20 mm below the annulus, 25 mm below the annulus, 30 mm below the annulus, 35 mm below the annulus, 40 mm below the annulus, 45 mm below the annulus, 50 mm below the annulus, 55 mm below the annulus, 60 mm below the annulus, 65 mm below the annulus, 70 mm below the annulus, 75 mm below the annulus, 80 mm below the annulus, 85 mm below the annulus, 90 mm below the annulus, 95 mm below the annulus, 100 mm below the annulus, 105 mm below the annulus, 110 mm below the annulus, 115 mm below the annulus, 120 mm below the annulus, 125 mm below the annulus, 130 mm below the annulus, 135 mm below the annulus, 140 mm below the annulus, 145 mm below the annulus, 150 mm below the annulus, 200 mm below the annulus, 250 mm below the annulus, or 300 mm below the annulus, or any range including two of the foregoing values. A distance below the annulus can reflect a distance below, for example, an inferior-facing surface of the annulus.

In some embodiments, the implant can be positioned and/or anchored in a superior zone of the left ventricle, such as, for example, up to midway (e.g., lengthwise) between the mitral valve annulus superiorly and the apex of the left ventricle inferiorly. In some embodiments, the implant can be positioned within the upper (e.g., superior-most) 50%, 45%, 40%, 35%, 30%, 25%, 20%, 15%, 10%, 5% of the left ventricle, or ranges including any two of the foregoing values. In some embodiments, the implant is not positioned in the inferior portion of the left ventricle.

The subannular implant can be positioned along the height of the posterior leaflet, for example within about 10% of the height of the posterior leaflet, 20% of the height of the posterior leaflet, 30% of the height of the posterior leaflet, 40% of the height of the posterior leaflet, 50% of the height of the posterior leaflet, 60% of the height of the posterior leaflet, 70% of the height of the posterior leaflet, 80% of the height of the posterior leaflet, 90% of the height of the posterior leaflet, 100% of the height of the posterior leaflet, or any range including two of the foregoing values. The subannular implant can be positioned along the radius of the annulus from the posterior leaflet to the ventricle wall, for example along within about 10% of the radius from the posterior leaflet, 20% of the radius from the posterior leaflet, 30% of the radius from the posterior leaflet, 40% of the radius from the posterior leaflet, 50% of the radius from the posterior leaflet, 60% of the radius from the posterior leaflet, 70% of the radius from the posterior leaflet, 80% of the radius from the posterior leaflet, 90% of the radius from the posterior leaflet, 100% of the radius from the posterior leaflet, from the posterior leaflet to the left ventricle, or any range including two of the foregoing values.

The subannular implant and the leaflet anchor implant can be guided toward the prolapsed segment of the mitral leaflet. The steering catheter can guide the subannular implant and the leaflet anchor implant along an arc. The steering catheter can guide the subannular implant and the leaflet anchor implant along a curve. The steering catheter can guide the subannular implant and the leaflet anchor implant along a radius of curvature.

In some embodiments, the leaflet anchor implant can include an attached tether. The tether can be coupled to the leaflet anchor implant through adhesive, tying, welding, and/or any other form of coupling. In some embodiments, the tether is integrally formed with the leaflet anchor implant. In some embodiments, the tether can be a suture, flexible cord, flexible wire, and/or any other tether. The leaflet anchor implant can be delivered to the free margin of the prolapsed segment of the leaflet. The proximal end of the tether can be gradually pulled through the subannular implant into the left atrium. Exerting tension, e.g., pulling on the tether can reduce the prolapse and the mitral regurgitation caused by the prolapsed mitral valve leaflet.

In some embodiments, a cinching catheter is advanced through the guiding catheter in the left atrium. The cinching catheter can be utilized to cinch, fix, and lock the tether and the subannular implant. In some embodiment, the cinching catheter can lock the tether and the subannular implant at a desirable length above and/or below the mitral annulus.

In some embodiments, a system of catheters is provided to deliver the subannular implant and the leaflet anchor implant to treat the mitral valve condition, such as prolapse. In some embodiments, a system of catheters is provided. In some embodiments, one or more mitral subannular implants are delivered alternatively in a retrograde manner via the femoral artery into the left ventricle. In some embodiments, a system of catheters is provided to steer the leaflet anchor implant and the subannular implant to reduce and treat the mitral valve prolapse. In some embodiments, an assembly is provided to pull both the anterior and the posterior mitral annulus towards each other. In some embodiments, the assembly is utilized with the above systems and restrains the systems above or below the mitral annulus to facilitate coaptation of the leaflets after treating the leaflet prolapse.

The disclosure relates generally to the field of heart valve repair devices, systems, methods, assemblies, and kits. The disclosure more specifically relates to, in some embodiments, transcatheter methods and devices for insertion of chords, sutures and other tethers, anchors, and implants to the mitral valve leaflets. The system and methods are utilized for reduction of the prolapsed mitral valve. The system and methods are utilized for the subannular fixation of the prolapsed leaflet to treat mitral valve regurgitation. In some embodiments, systems and method can also be utilized to treat tricuspid, or other valvular prolapse or regurgitation.

The heart has a total of four valves (e.g., the mitral, tricuspid, aortic, and pulmonic valves) which allows the blood to flow through the four chambers of the heart in one direction. The mitral valve has two valve leaflets, anterior and posterior. The leaflets are attached to the mitral valve annulus. The leaflets are normally supported by chordae tendinae from their free edges towards the wall of the left ventricle by the papillary muscles. Normally when the left ventricle contracts, the leaflets close together preventing blood to leak backwards into the left atrium, which is the upper pumping chamber. Sometimes one or both leaflets do not close properly as a result of excess leaflet tissue, elongated or torn chordae tendinae, dilated mitral valve annulus, or a combination of these conditions. The valve then prolapses back into the left atrium and the blood leaks back into the left atrium during systole or cardiac contraction. This condition is called mitral regurgitation. The blood backs up into the lungs which is directly connected through pulmonary veins. This causes heart failure. This also causes the lungs to become waterlogged causing shortness of breath on exertion, orthopnea, jugular venous distention, and/or other symptoms.

Several treatment modalities have been performed by either replacing the entire mitral valve with an artificial valve or repairing the valve by shortening the chordae tendinae or insertion of new chords on to the papillary muscles inside the left ventricular cavity. Many of these solutions are surgical and invasive. There is still a need for less invasive non-surgical transcatheter solutions to avoid the risks of major surgical treatments, including therapies that preserve the native valve.

There have been less invasive trans-apical approaches to insert new chords to the prolapsed leaflets, with reduction of prolapse resulting from attachment of these chords onto the surface of the left ventricle, instead of the papillary muscle inside the left ventricular cavity. While this procedure is performed without opening the heart chambers and thus avoids use of a heart lung machine and stopping the heart, this procedure still require open surgical access in the left side of the chest to expose the left ventricular apex. As such, some embodiments do not involve repairing or replacing existing chordae tendinae, and/or do not involve attachment of any system elements to papillary muscles.

Recently transcatheter trans-septal closed chest transvascular techniques and devices have been proposed to insert new chords to the prolapsed leaflet and attach these chords to the papillary muscle in the wall of the left ventricle inside the left ventricular cavity. This procedure requires challenging echo imaging to localize these papillary muscles and has the potential for detachment of these anchors in the papillary muscles.

Therefore, there is a need for simpler, more practical, less risky methods for reducing leaflet prolapse. In some embodiments, systems and methods are provided that involve one or more robust locations for anchoring the new leaflet chords, sutures, or any other tethers. In some embodiments, systems and methods are provided that involve easy visualization of the one or more anchoring locations. In some embodiments, systems and methods are provided that allow robust and simple anchoring methods and devices within the left ventricular chamber, such as the very uppermost portion of the left ventricular chamber in the subannular region.

Described here are methods, implants, and systems for treatment of mitral valve prolapse by attaching one or more flexible tethers between the prolapsed leaflet and the mitral annulus. Described here are methods, implants, and systems for treatment of mitral valve prolapse by adjusting the length of these one or more tethers to reduce the prolapse of the leaflet. Some embodiments do not involve implantation of annuloplasty rings, or substantially change the size or shape of the native valve annulus. Some embodiments do not involve positioning a bridge implant across the native valve annulus.

In some embodiments, the method comprises advancing the guiding catheter percutaneously from femoral vein into the right atrium, through the fossa ovalis into the left atrium and through this catheter introducing a steerable stabilizing template catheter onto the mitral annulus. In some embodiments, a piercing needle is advanced inside the steerable stabilizing template catheter and the mitral annulus is pierced. In some embodiments, the method can include advancing the piercing needle to the subannular space underneath the annulus. In some embodiments, a guide wire is passed through the hollow part of this piercing needle. In some embodiments, subsequently over this guide wire the steerable catheter is passed towards the prolapsed leaflet.

The steerable catheter can advance the leaflet anchor implant with the attached tether. The leaflet anchor implant can be deployed to secure to the prolapsed mitral valve leaflet. Following this step, the subannular implant can be advanced over the tether to the prolapsed leaflet. The tether can be gradually pulled through the subannular implant to move the subannular implant towards the subannular location immediately beneath the mitral annulus. The subannular implant can be positioned to reduce the prolapse. In some embodiments, the mitral regurgitation is eliminated as observed, in real time, in a beating heart using Doppler echocardiography or other imaging techniques.

After the desired reduction of prolapse is achieved, the tether of the leaflet anchor implant can be cinched. The tether can be secured on to the mitral annulus by a suture lock. The excess tether can be cut above the mitral annulus. In some embodiments, all the steering catheters and the trans-septal guiding catheters are removed completing the procedures.

The tether, the leaflet anchor implant, and the subannular implant can be made of an appropriate biocompatible material, such as a metal, shape memory metal, plastics, shape memory plastic, non-polymeric fabrics, polymers, nickel titanium alloy, and combinations thereof. The subannular implant can be of various sizes to achieve various degrees of adjustment of the tether at various angles below the valve leaflet. The subannular implant can be made of, for example, springs, tubes made of nickel titanium alloy, various polymers, and/or stainless steel. The leaflet anchor implant also can be made from polymers, stainless steel, nickel titanium alloys, and other materials or combinations of materials including those disclosed elsewhere herein.

In some embodiments, following the placement of the guiding catheter in the left atrium via a trans septal access from the femoral vein, the steerable stabilizing template catheter is advanced through the mitral orifice to the undersurface of the mitral annulus facing the left ventricle. The annular piercing needle is advanced through the steerable stabilizing template catheter into the left atrium followed by a passing a guide wire into the left atrium. A basket catheter is passed over the guide wire into the left atrium above the mitral annulus. Through the already placed guiding catheter in the left atrium, another guide wire is passed towards the basket catheter. This guide wire can be captured by the basket catheter and withdrawn through the femoral vein completing a wire loop through the heart chamber e.g., right atrium to left atrium and back to right atrium. With the guide wire through the mitral annulus, the rest of the steps can be completed as described above and the leaflet anchor implant and the subannular implant can positioned in the subannular space with reduction in prolapse.

Alternatively, access to the mitral annulus can be obtained by a retrograde approach from the femoral artery to position the leaflet anchor implant, position the subannular implant, and adjust the tether to reduce the prolapse.

FIG. 1 shows an embodiment of a guiding catheter 100 in the left atrium. The heart includes a prolapsed leaflet. FIG. 1 also shows the subannular implant 102 and the leaflet anchor implant 104. The subannular implant 102 can be a tubular structure. The subannular implant 102 can have a lumen. The subannular implant 102 can have a first open end and a second open end. The subannular implant 102 can be linear. The subannular implant 102 can be non-linear. The subannular implant 102 can be flexible. The subannular implant 102 can be rigid. The subannular implant 102 can have a preformed shape. The subannular implant 102 can have a preformed radius of curvature. The subannular implant 102 can have a predetermined length. The subannular implant 102 can be made of any biocompatible material. The subannular implant 102 can have a shape to fit below the annulus. The subannular implant 102 can have a shape to hold the prolapsed leaflet in a predetermined position.

The leaflet anchor implant 104 can be disposed on the prolapsed leaflet. The subannular implant 102 and the leaflet anchor implant 104 can be coupled on either side of the prolapsed leaflet. The tether 106 can be coupled to the leaflet anchor implant 104. The tether 106 can extend through the leaflet anchor implant 104. The tether 106 can extend from one side of the leaflet anchor implant 104. The tether 106 can extend through the prolapsed leaflet. The tether 106 can extend through the subannular implant 102. The subannular implant 102 can be guided toward the leaflet anchor implant 104. The tether 106 can extend through the annulus. The tether 106 can extend through the suture lock 108. The tether 106 can extend through the guiding catheter 100.

FIG. 1 also shows the tether 106 and the suture lock 108. The tether 106 can be coupled to the leaflet anchor implant 104. The tether 106 can pass through the subannular implant 102. The tether 106 can be locked by the suture lock 108. The tether 106 can be locked by the suture lock 108 underneath the annulus. The suture lock 108 can define the length of the tether 106 between the leaflet anchor implant 104 and the annulus. The suture lock 108 can define the length of the tether 106 that extends through the subannular implant 102. The tether 106 can be locked by the suture lock 108 above the annulus. The suture lock 108 can define the length of the tether 106 that extends through the annulus. Any combination of sutures locks 108 can be utilized. In some methods, only one suture lock 108 is utilized. In some methods, only one suture lock 108 above the annulus is utilized. In some methods, only one suture lock 108 below the annulus is utilized.

The tether 106 can be tightened in use. The tether 106 can be tightened, thereby positioning the subannular implant 102 in the subannular space between the annulus and the prolapsed leaflet. The tether 106 can be tightened, thereby positioning the subannular implant 102 against the prolapsed leaflet. The tether 106 can be tightened, thereby positioning the subannular implant 102 against the underside of the annulus. The suture lock 108 can secure the tether 106 after tension is applied.

The subannular implant 102 can form a curve in the subannular space. The subannular implant 102 can form a curve from the location of the leaflet anchor implant 104 to the suture lock 108. The tether 106 can be coupled with both the leaflet anchor implant 104 and the subannular implant 102. The tether 106 can be coupled with the suture lock 108. One or more suture locks 108 can be provided. One or more suture locks 108 can be positioned above the mitral annulus. One or more suture locks 108 can be positioned, instead or additionally, below the mitral annulus. In the illustrated embodiment, one suture lock 108 is positioned both above and below the mitral annulus.

The subannular implant 102 can be flexible. The subannular implant 102 can be rigid in other cases. The subannular implant 102 can maintain its shape. The subannular implant 102 can have a shape memory shape. The subannular implant 102 can be formed from any of a variety of materials, including various polymers and metals including titanium, titanium alloy, Nitinol, stainless steel, or other metals known in the art. The subannular implant 102 may be treated or coated with a suitable material to eliminate the effects of thrombosis or corrosion. The subannular implant 102 can have a flared configuration. The subannular implant 102 can include features to abut the anatomy. The subannular implant 102 can include a flared end to distribute force on the leaflet. The subannular implant 102 can include a flared end to distribute force on the annulus. The subannular implant 102 can provide a relatively large footprint relative to the annulus and/or the prolapsed leaflet. The subannular implant 102 can have a reduced diameter or cross-sectional shape along the length of the subannular implant 102. The subannular implant 102 can have any profile. The subannular implant 102 can be nonporous. The subannular implant 102 can be porous.

The subannular implant 102 can have several advantages. The subannular implant 102 can provide support to the prolapsed leaflet during systole. The subannular implant 102 can hold the leaflet in position. The subannular implant 102 can change the point of coaptation. The subannular implant 102 can change the plane of coaption. The subannular implant 102 can change the shape of a coaptation surface. The subannular implant 102 can replicate the proper spatial location of coaptation by repositioning the prolapsed leaflet. The subannular implant 102 can move the prolapsed leaflet toward the other leaflet of the valve. In some embodiments, the prolapsed leaflet can have limited movement when supported by the subannular implant 102.

The subannular implant 102 can have several additional advantages. The subannular implant 102 can prevent the leaflet from prolapsing. The subannular implant 102 can provide a restraining force. The subannular implant 102 can prevent the leaflet from traveling above the plane of the annulus.

The subannular implant 102 can have several advantages compared with other implants. The subannular implant 102 can couple to sturdy anatomy including the annulus and the leaflet. The subannular implant 102 can be positioned in the subannular space and well above the chordae and papillary muscle sites of attachment. The subannular implant 102 does not obstruct the flow of blood in some cases. The subannular implant 102 is not positioned in the mitral valve orifice in some cases.

The subannular implant 102 can be configured to be compressed for delivery. The subannular implant 102 can be under compression when implanted. The subannular implant 102 can be under compression by the leaflet anchor implant 104 and the suture lock 108. The subannular implant 102 can be expanded within the heart. The subannular implant 102 can be transformed from a radially reduced configuration for delivery to a radially enlarged configuration for positioning within the heart. The subannular implant 102 can be compressed within a delivery catheter. The subannular implant 102 can be compressed to fit through a pierced hole in the annulus. The subannular implant 102 can be expanded to prevent regression through the pierced hole in the annulus.

The leaflet anchor implant 104 can be configured to be compressed for delivery. The leaflet anchor implant 104 can be under tension when implanted. The leaflet anchor implant 104 can be under tension by tension applied by the tether 106. The leaflet anchor implant 104 can be expanded within the heart. The leaflet anchor implant 104 can have a low profile configuration and a larger profile configuration. The leaflet anchor implant 104 can transform between configurations by rotation of the implant, e.g., a horizontal orientation through a pierced hole and a vertical orientation once positioned against the leaflet. The leaflet anchor implant 104 can be compressed within a delivery catheter. The leaflet anchor implant 104 can be compressed to fit through a pierced hole in the annulus. The leaflet anchor implant 104 can be compressed to fit through a pierced hole in the leaflet. The leaflet anchor implant 104 can be expanded to prevent regression through the pierced hole in the leaflet.

In some embodiments, the suture lock 108 can be configured to be compressed for delivery. The suture lock 108 can hold the tether 106 under tension once implanted. The suture lock 108 can be positioned within the subannular space. The suture lock 108 can be positioned within the annulus. The suture lock 108 can be transformed from a radially reduced configuration for delivery to a radially enlarged configuration for positioning within the subannular space. The suture lock 108 can be compressed to fit through a pierced hole in the annulus if delivered to the subannular space. The suture lock 108 can be configured to prevent regression of the subannular implant 102 through the pierced hole in the annulus. The tether could be elastic, or nonelastic in some embodiments.

In some embodiments, the subannular implant 102 is entirely below the surface of the annulus. In some embodiments, the subannular implant 102 is entirely within the subannular space. In some embodiments, the subannular implant 102 is entirely in the left ventricle. In some embodiments, the subannular implant 102 extends in an arc between the annulus and the prolapsed leaflet. In some embodiments, the leaflet anchor implant 104 is entirely in the mitral valve orifice. In some embodiments, the leaflet anchor implant 104 is entirely outside of the subannular space. In some embodiments, the suture lock 108 is entirely in the left atrium. In some embodiments, a suture lock 108 is within the left ventricle and a suture lock is within the left atrium. In some embodiments, the suture lock 108 is entirely above the surface of the annulus.

In some embodiments, the subannular implant 102 is expandable. In some embodiments, the leaflet anchor implant 104 is expandable. In some embodiments, the suture lock 108 is expandable. The subannular implant 102, leaflet anchor implant 104 and/or suture lock 108 can be self-expandable. The subannular implant 102, leaflet anchor implant 104 and/or suture lock 108 can expand upon removal of a constraint. The subannular implant 102, the leaflet anchor implant 104 and/or the suture lock 108 can expand after being passed through an opening. The leaflet anchor implant 104 can expand after being passed through an opening in the leaflet. The subannular implant 102 can expand after being passed through an opening in the annulus. The suture lock 108 can expand after being passed through an opening in the annulus for the sub annular suture lock 108. The suture lock 108 can expand after being passed through an opening in the guide catheter for the suture lock 108 above the annulus.

In some embodiments, the subannular implant 102 is selected from a plurality of subannular implants having different shapes. In some embodiments, the subannular implant 102 is selected from a plurality of subannular implants having different flexibilities. In some embodiments, the subannular implant 102 is selected from a plurality of subannular implants having different lengths. In some embodiments, the leaflet anchor implant 104 is selected from a plurality of leaflet anchor implant 104 that have different anchoring characteristics. In some embodiments, the leaflet anchor implant 104 is selected from a plurality of leaflet anchor implant 104 that have different diameters or cross-sectional dimensions. In some embodiments, the leaflet anchor implant 104 is selected from a plurality of leaflet anchor implant 104 that have different tethers 106 coupled thereto. In some embodiments, the tether 106 is selected from a plurality of tethers 106. In some embodiments, the suture lock 108 is selected from a plurality of suture locks 108. In some embodiments, the suture lock 108 above the annulus is the same as the suture lock 108 below the annulus. In some embodiments, the suture lock 108 above the annulus has different features from the suture lock 108 below the annulus.

Figure 2:
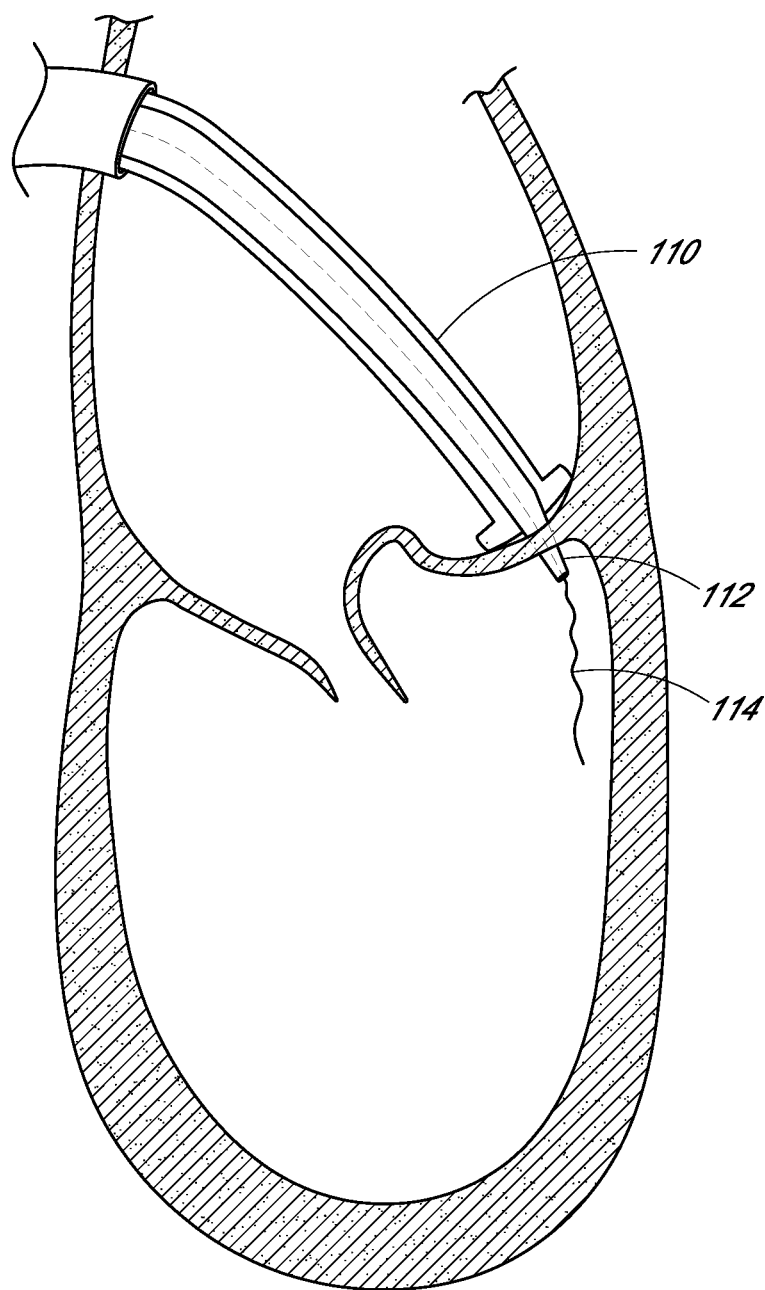
FIG. 2 shows an embodiment of a steerable stabilizing template catheter.

FIG. 2 shows a steerable stabilizing template catheter 110 on the annulus. In some embodiments, a piercing needle 112 is provided. The piercing needle 112 can be passed through the steerable stabilizing template catheter 110 positioned on the annulus. The piercing needle 112 can be passed through the mitral annulus. The piercing needle 112 can be passed into the subannular location. The piercing needle 112 can be passed to the space below the annulus. Once positioned in the subannular space, a guide wire 114 can be passed through a tip of the piercing needle 112. The guide wire 114 can exit from the tip of the piercing needle 112. The systems can be utilized with any device the forms an opening in the annulus. The piercing needle 112 can apply heat to cauterize the opening. In some embodiments, the piercing needle 112 forms an opening in the leaflet.

Figure 3A:
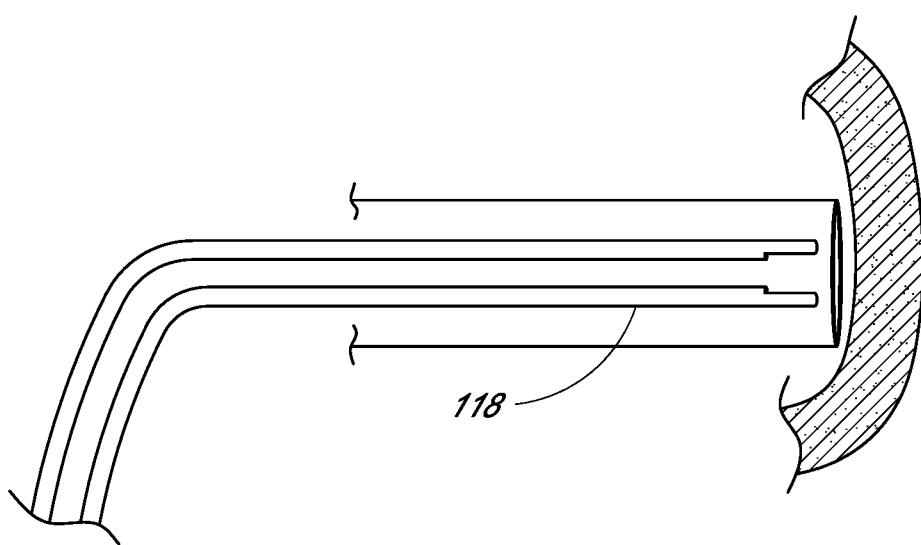
FIGS. 3A-3C show advancement of the steerable stabilizing template catheter of FIG. 2.
Figure 3B:
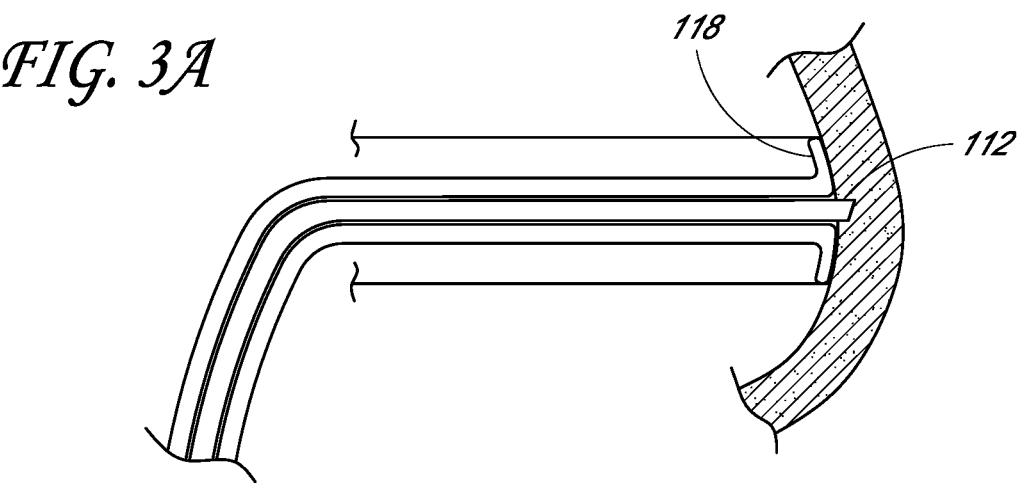
Figure 3C:
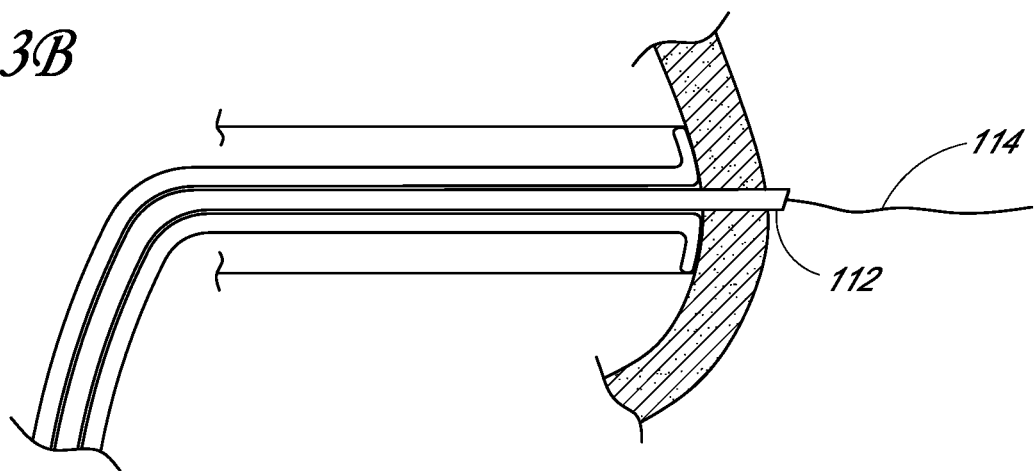

FIG. 3A shows steps of advancing a template 118 of the steerable stabilizing template catheter 110 through the guiding catheter 100. FIG. 3B shows the template 118 of the steerable stabilizing template catheter 110 opened on to the annulus. FIG. 3B also shows the piercing needle 112 beginning to penetrate the annulus. FIG. 3C shows the piercing needle 112 through the annulus and in the subannular space. The guide wire 114 is shown exiting the piercing needle 112. The steerable stabilizing template catheter 110 can include legs that flex. The steerable stabilizing template catheter 110 can include legs that are initially straight as shown in FIG. 3A. The steerable stabilizing template catheter 110 can include legs that deflect and rest against the annulus as shown in FIG. 3B. The flexed legs of the steerable stabilizing template catheter 110 can provide a countering force as the needle penetrates the annulus.

Figure 4A:
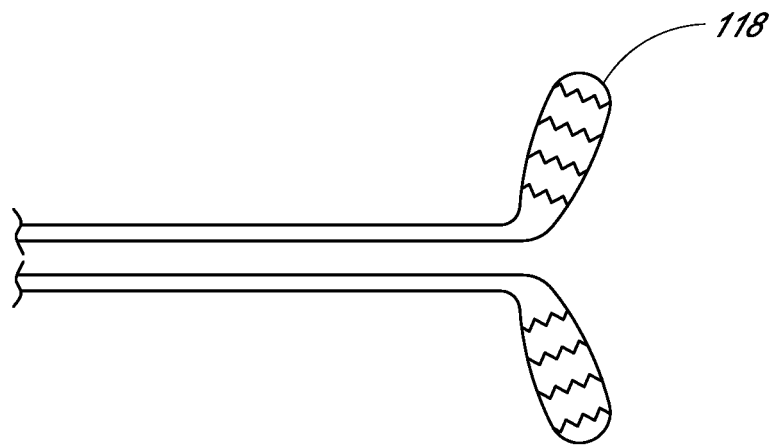
FIGS. 4A-4B show embodiments of surfaces of the steerable stabilizing template catheter of FIG. 2.
Figure 4B:
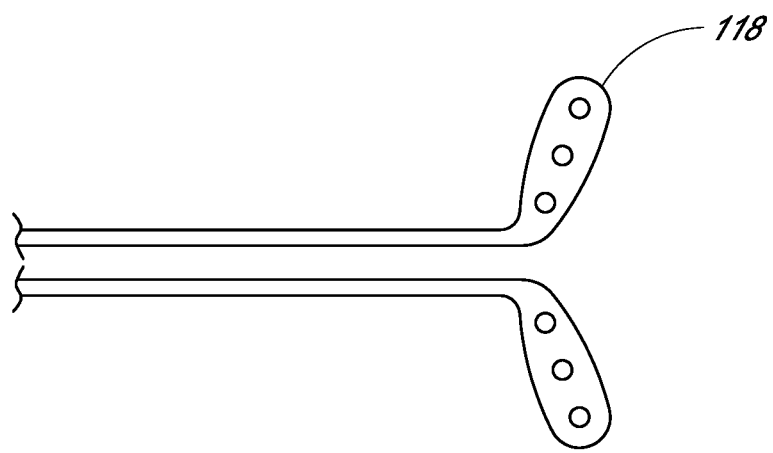

FIGS. 4A-4B show surfaces of the template 118. The steerable stabilizing template catheter 110 can have any surface feature. The legs of the steerable stabilizing template catheter 110 can have features to enhance the grip on the annulus. FIG. 4A shows rough ridges on the template 118. FIG. 4B shows suction pods on the template 118. The template 118 can have any configuration to facilitate gripping the surface of the annulus.

Figure 5:
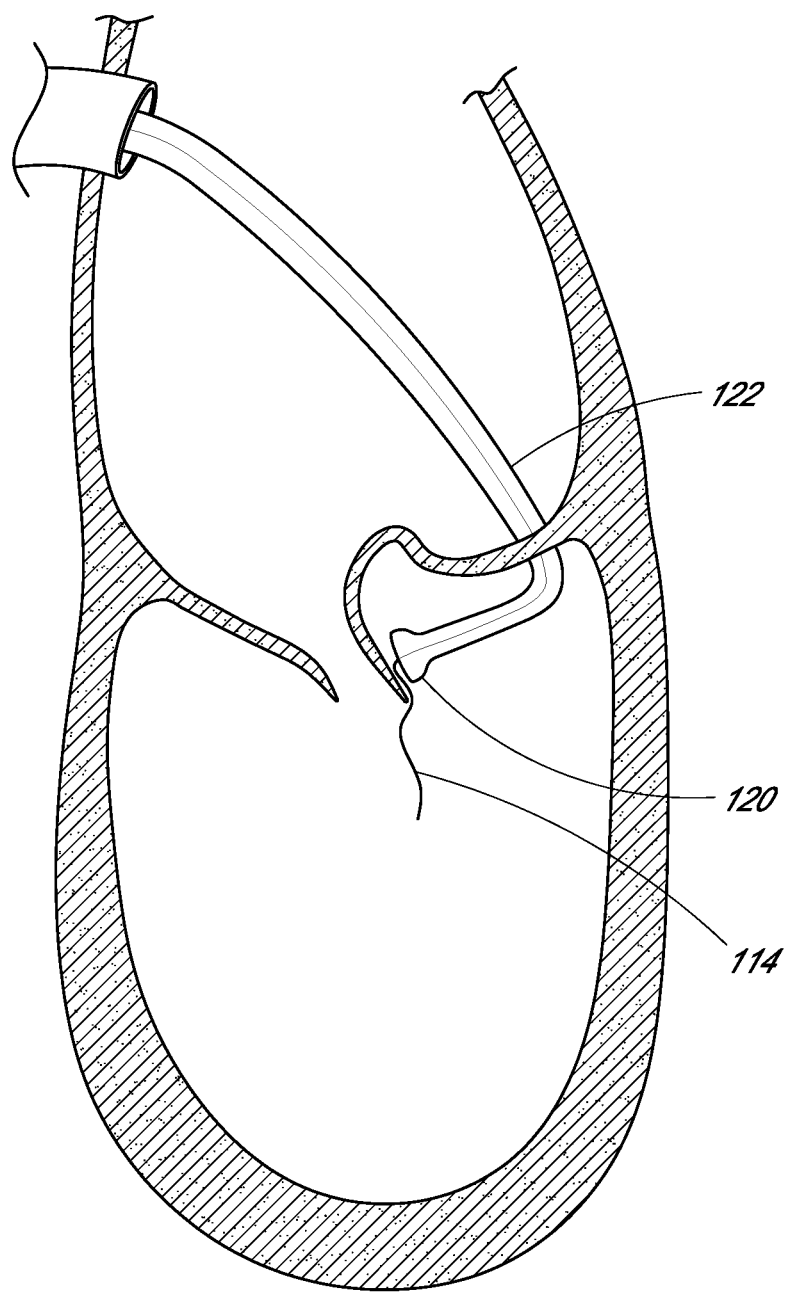
FIG. 5 shows an embodiment of a leaflet capturing element.

FIG. 5 shows a leaflet capturing element 120. The leaflet capturing element 120 can have any feature to grip the leaflet. The leaflet capturing element 120 can have any feature of any catheter described herein. The leaflet capturing element 120 can have a flared end to contact the leaflet. The leaflet capturing element 120 can include ridges or suction pods to grip the leaflet. The leaflet capturing element 120 can be configured to grasp or hold the leaflet to allow the leaflet to be penetrated. The leaflet capturing element 120 can hold the leaflet as an opening is formed through the leaflet. The leaflet capturing element 120 can be advanced with a steering catheter 122. The steering catheter 122 can be flexible. The steering catheter 122 can be controlled. The steering catheter 122 can deliver the leaflet anchor implant 104. The steering catheter 122 can pass the leaflet anchor implant 104 through the opening the leaflet. The steering catheter 122 can move relative to the leaflet capturing element 120 to deliver the leaflet anchor implant 104. The leaflet anchor implant 104 can be positioned within the steering catheter 122. The steering catheter 122 can be guided toward the leaflet by the guide wire 114. The steering catheter 122 moves within the subannular space toward the prolapsing leaflet. The steering catheter 122 can position the leaflet anchor implant 104.

Figure 6:
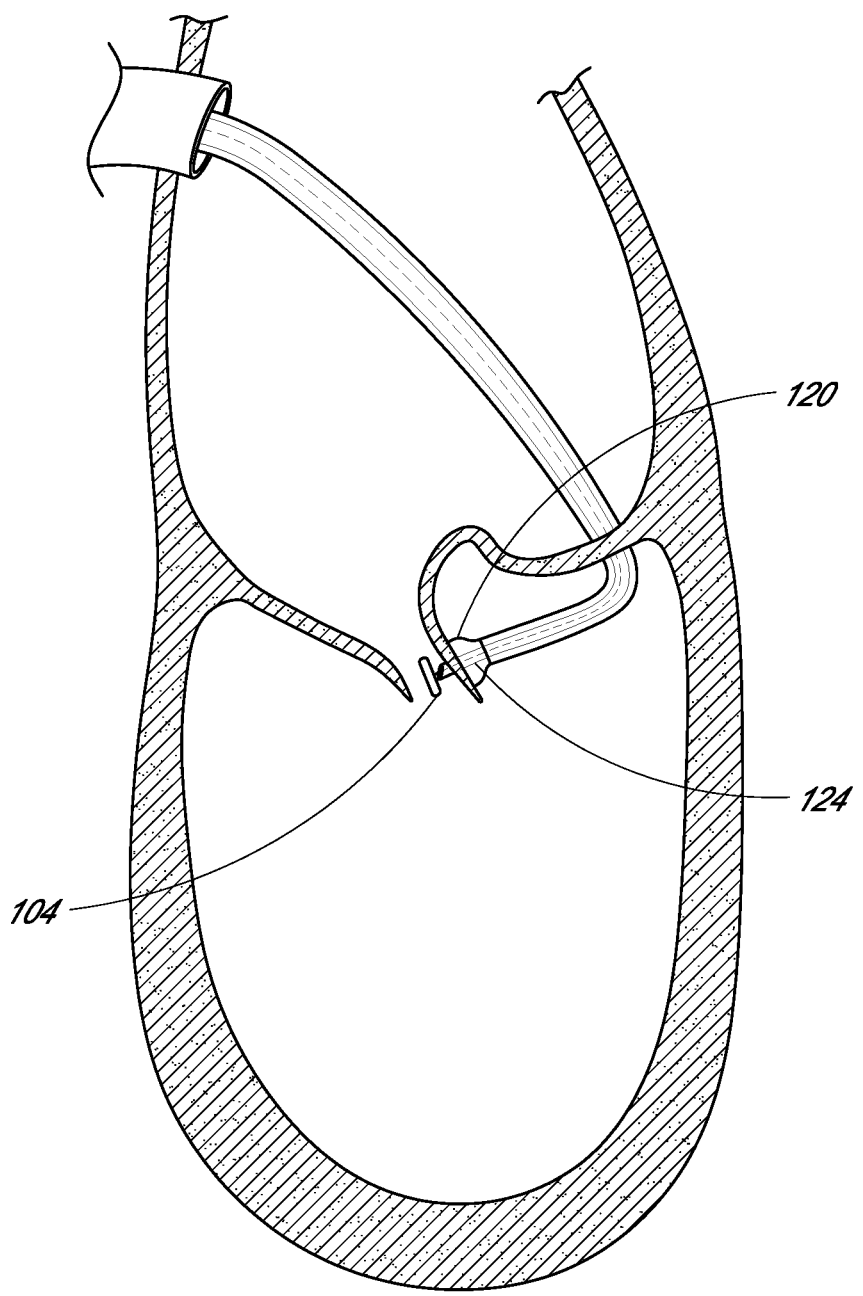
FIG. 6 shows an embodiment of a leaflet anchor implant and the leaflet capturing element of FIG. 5.

FIG. 6 shows the leaflet anchor implant 104 through the leaflet. In some embodiments, a leaflet piercing needle 124 is delivered through the steering catheter 122. The leaflet piercing needle 124 can pierce through the leaflet from the subannular space toward the mitral valve orifice. In some embodiments, the leaflet piercing needle 124 can form the hole in the leaflet. In some embodiments, the steering catheter 122 can pass the leaflet anchor implant 104 through a hole formed by the leaflet piercing needle 124. The leaflet anchor implant 104 can be delivered through the pierced leaflet. The leaflet capture element 120 can capture the leaflet as the leaflet is being pierced. The leaflet capture element 120 can hold the leaflet as the leaflet anchor implant 104 is delivered. The leaflet anchor implant 104 can be positioned within the valve. The leaflet anchor implant 104 on the other side of the leaflet. The leaflet anchor implant 104 is opposite the subannular space. The leaflet anchor implant 104 can be positioned below the coaptation surface of the leaflet. The leaflet anchor implant 104 is positioned below the valve plane. The leaflet anchor implant 104 can abut a surface of the leaflet.

Figure 7:
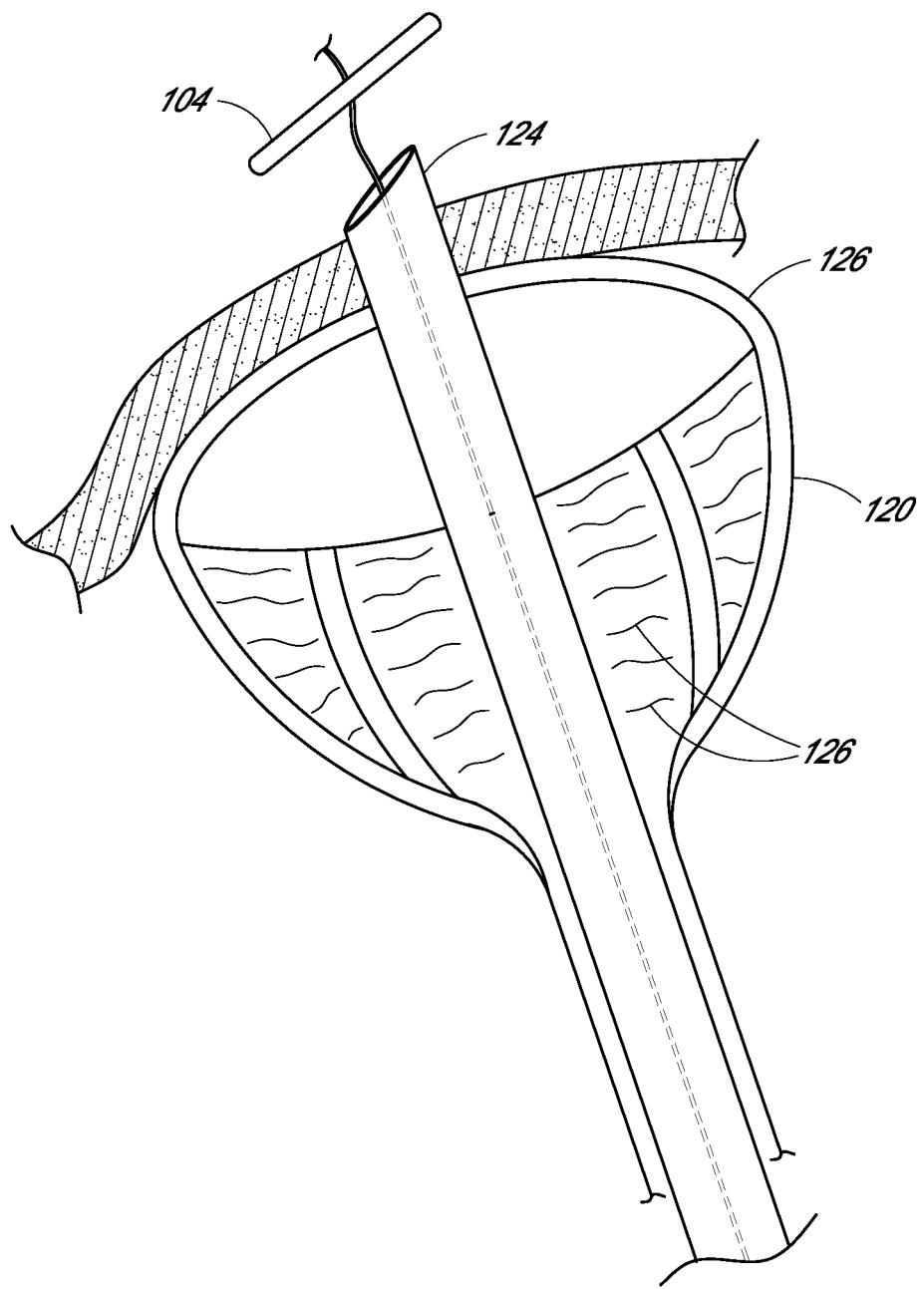
FIG. 7 shows the leaflet capturing element of FIG. 5.

FIG. 7 shows an enlarged view of an embodiment of the leaflet capturing element 120. The leaflet capture element 120 can include features 126. The features 126 can include ribs. The features 126 can include webs or webbing. The features 126 can include rough surfaces. The features 126 can include an expandable elements. The features 126 can include an inflatable balloon to capture and fix the leaflet. The features 126 can include any combination of features. FIG. 7 also shows the leaflet anchor implant 104 positioned relative to the leaflet, as well as the leaflet piercing needle 124. FIG. 7 shows various features of the leaflet capturing element 120.

Figure 8A:
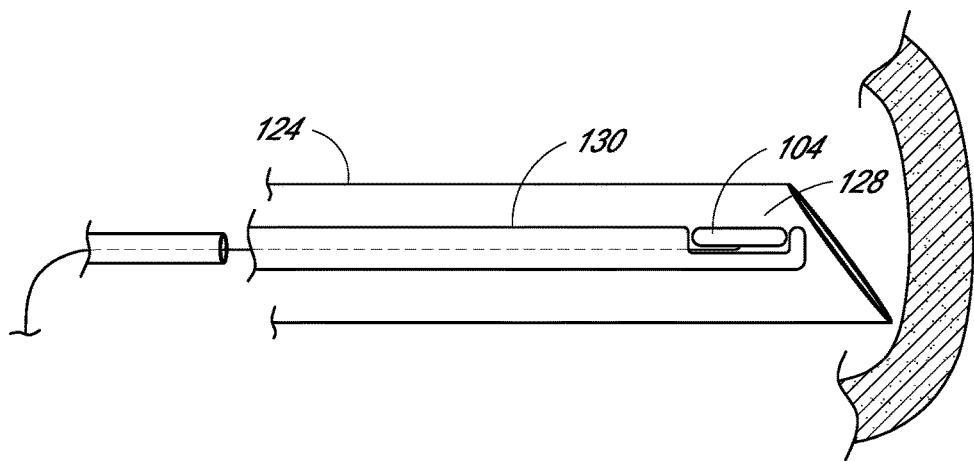
FIGS. 8A-8C show an embodiment of a leaflet anchor implant delivery.
Figure 8B:
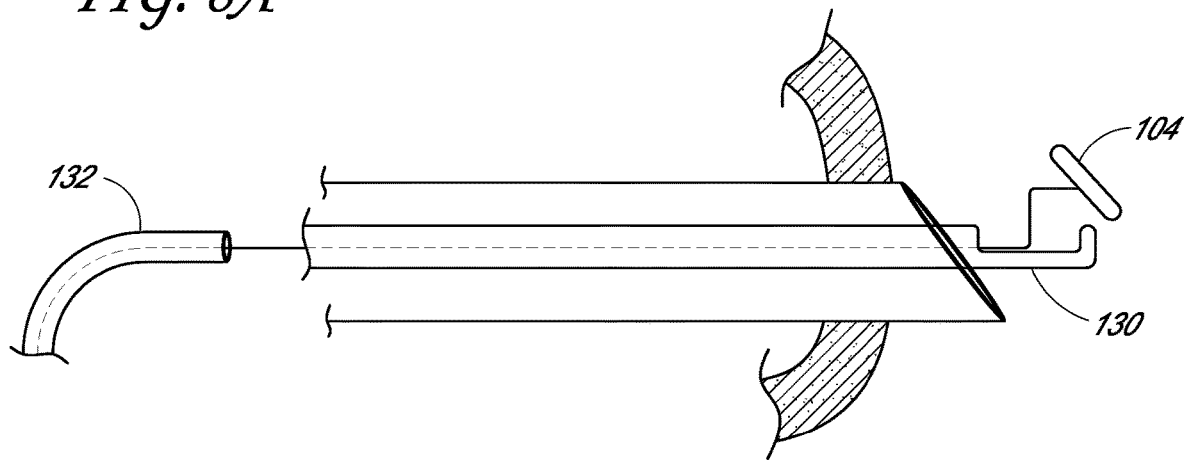
Figure 8C:
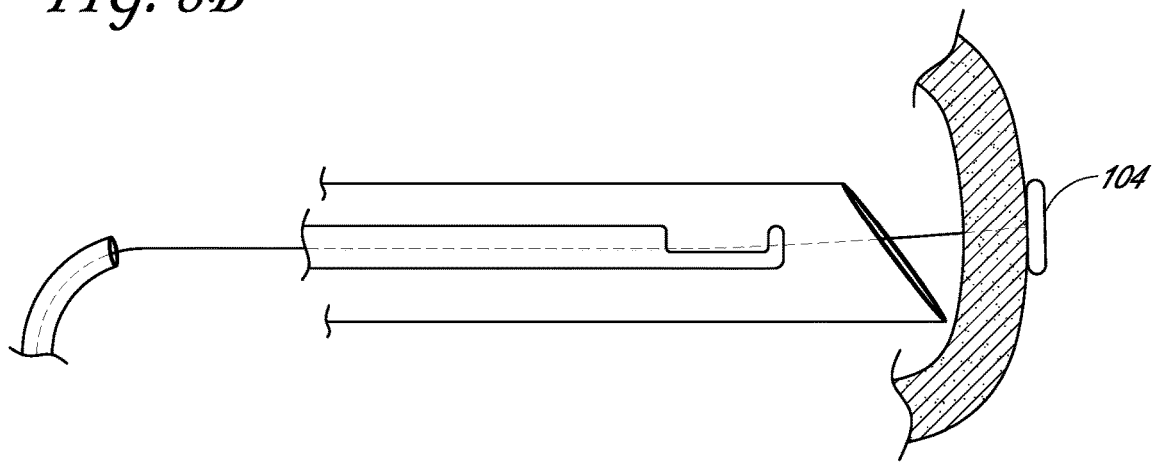

FIGS. 8A-8C shows delivery of the leaflet anchor implant 104 according to some embodiments, including the actual leaflet anchor delivery through the leaflet after the leaflet is captured, or de novo penetration of the leaflets. The system can include the leaflet piercing needle 124 that pierces the leaflet. The system can include leaflet implant catheter 130. The leaflet implant catheter 130 can deliver the leaflet anchor implant 104. The leaflet implant catheter 130 can include a housing 128. The leaflet implant catheter 130 can include a cutout in the housing 128 to deliver the leaflet anchor implant 104. The leaflet implant catheter 130 can include a pusher catheter 132 to deploy the leaflet anchor implant 104. The pusher catheter 132 can slide relative to the leaflet implant catheter 130. FIG. 8A shows the leaflet piercing needle 124 with the cutout leaflet anchor implant housing 128 of the leaflet implant catheter 130. FIG. 8B shows the pusher catheter 132 pushing the leaflet implant catheter 130 with the leaflet anchor implant 104 through the leaflet piercing needle 124 and the leaflet. In some embodiments, the leaflet anchor implant 104 is pushed into the valve. In some embodiments, the leaflet anchor implant 104 is pushed into the space between the leaflets. In some embodiments, the leaflet anchor implant 104 is pushed into to the annulus (not shown) and in the subannular space (not shown). FIG. 8C shows the leaflet piercing needle 124 and the leaflet implant catheter 130 withdrawn from the annulus with leaflet anchor implant 104 delivered and against the leaflet surface.

Figure 9A:
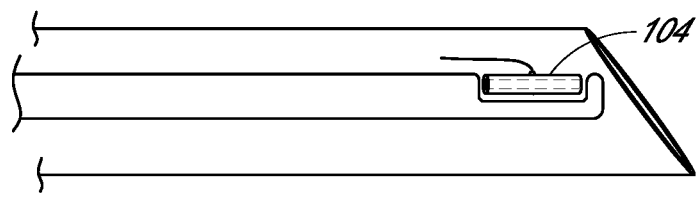
FIGS. 9A-9C show embodiments of the leaflet anchor implant.
Figure 9A:
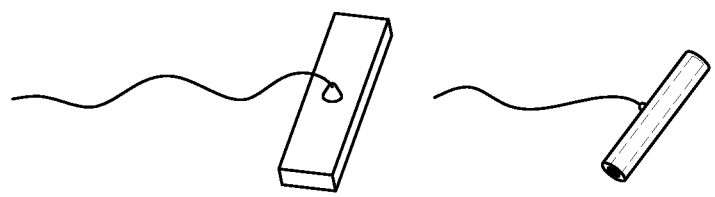
Figure 9B:
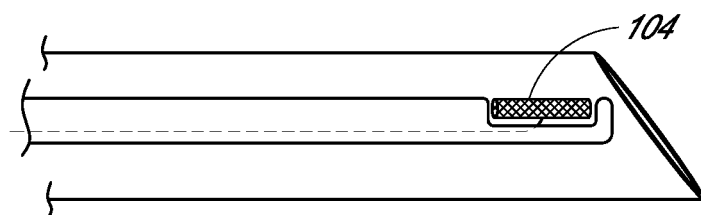
Figure 9C:
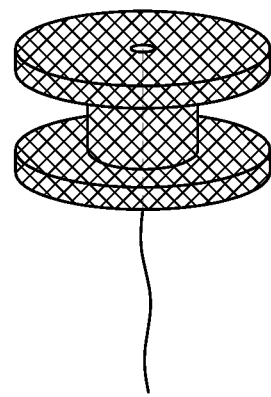
Figure 9C:
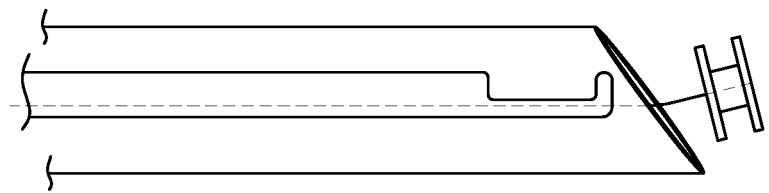
Figure 10A:
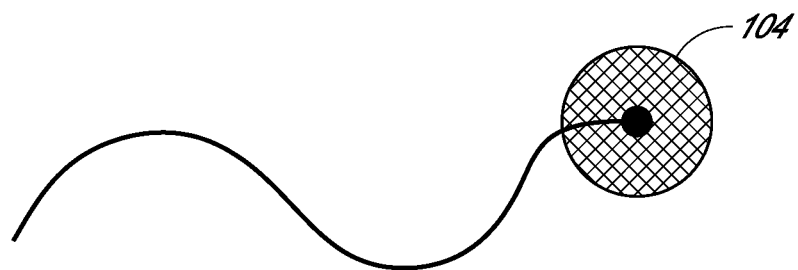
FIGS. 10A-10B show embodiments of the leaflet anchor implant.
Figure 10B:
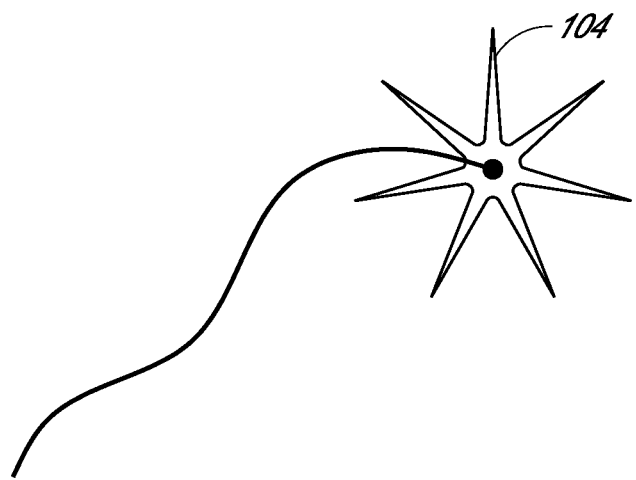

FIGS. 9A-9C show non-limiting embodiments of various types of leaflet anchor implants 104. FIG. 9A shows a rolled pledget form factor. The pledget can be rolled for delivery and expanded once positioned relative to the anatomy. The leaflet anchor implants 104 can expand to the preformed shape. The leaflet anchor implants 104 can be rectangular. The leaflet anchor implants 104 can be compressed in width and/or length. FIG. 9B shows the leaflet anchor implants 104 rolled with dumb bell shaped disk implant. FIG. 9C shows a "dumb bell" shaped disc implant. The dumb bell disc implant can be compressed or rolled for delivery and expanded in situ. The dumb bell disc implant can include a top part with an enlarged diameter, a waist with a smaller diameter, and a bottom part with an enlarged diameter that can be the same as, or different from the top part. In some embodiments, the leaflet implant could be a T-bar/T-tag implant that can have a transversely reduced configuration when delivered to the desired anatomic site and a transversely enlarged configuration after delivery. For example, the implant can be linear when housed within the leaflet implant housing 128 and can become horizontal after it has passed through the leaflet, e.g., actuated by an actuator at the tip of the delivery catheter FIGS. 10A-10B show more embodiments of the leaflet anchor implant 104. FIG. 10A shows a single disc coupled at one end of a tether 106. FIG. 10B shows a star shaped implant coupled at one end of a tether 106. The leaflet anchor implants 104 can expand to any shape. The leaflet anchor implants 104 can have any enlarged footprint. leaflet anchor implants 104 can have dimensions larger than the pierced hole to prevent retraction into the subanuuluar space.

Figure 11C:
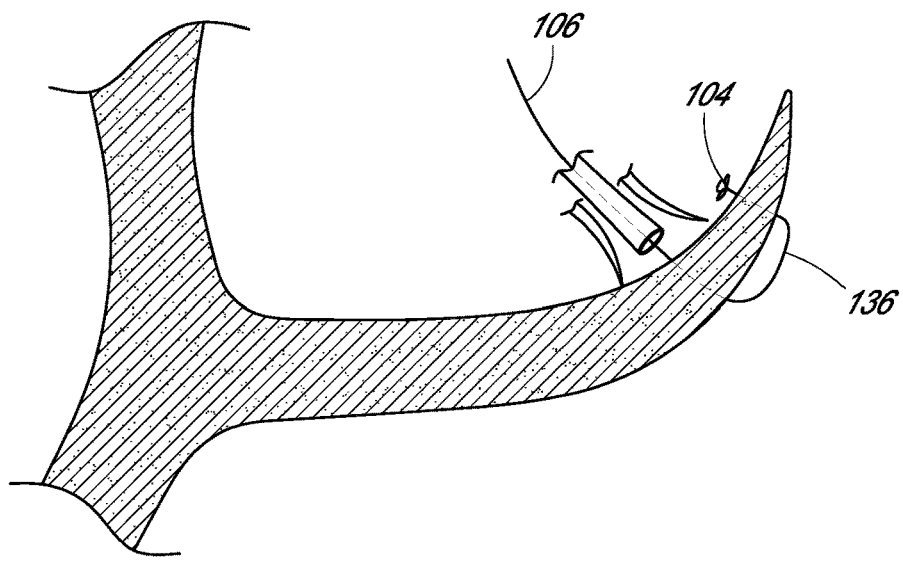
FIGS. 11A-11C show an embodiment of the leaflet anchor implant delivery.
Figure 11B:
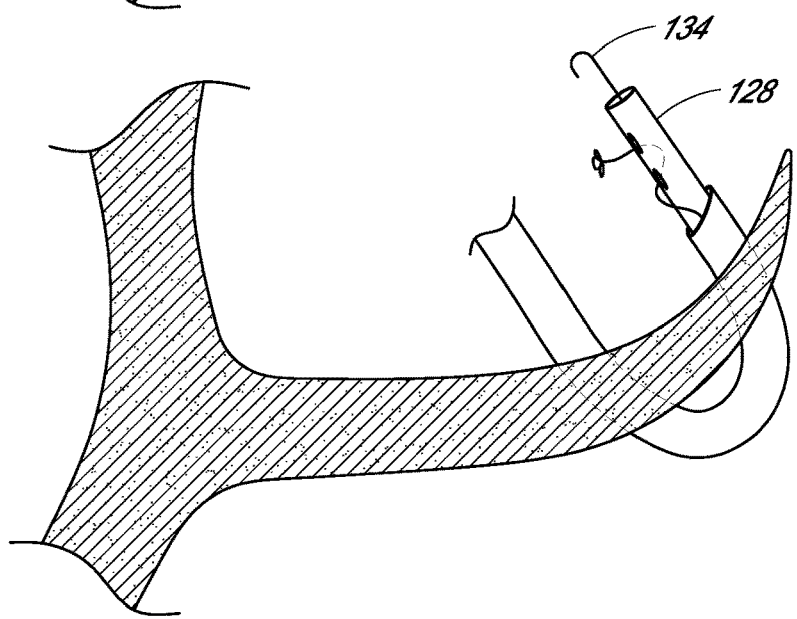
Figure 11A:
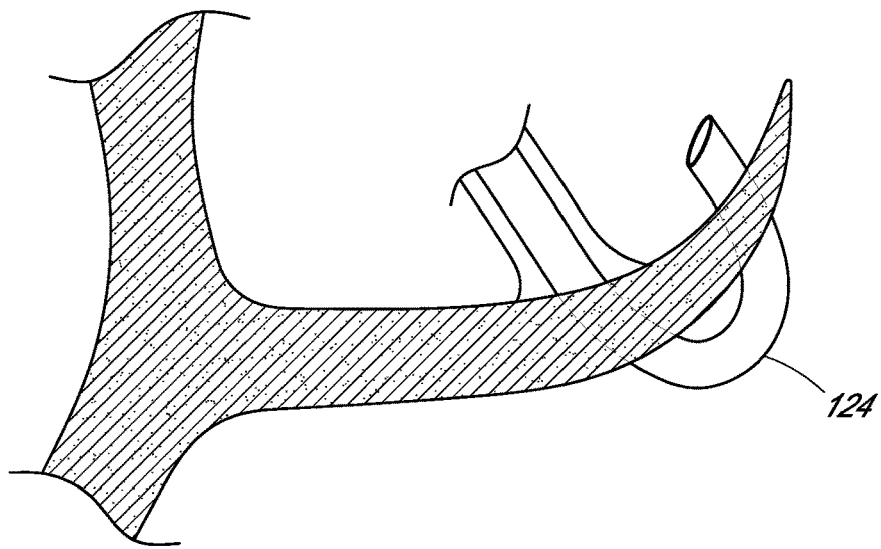

FIGS. 11A-11C show another embodiment of a leaflet anchor implant 104. FIG. 11A shows the leaflet piercing needle 124 passed through the leaflet. FIG. 11B shows the needle 132 across the leaflet with the leaflet anchor implant housing 128 with holes for the suture. FIG. 11B also shows a guide wire 134. FIG. 11B shows a mattress suture 136 with a simple single knot. FIG. 11C shows the mattress suture 136 delivered through the leaflet with the simple single knot at one end and the tether 106 at the other end. In some embodiments, the leaflet piercing needle can come from either, for example, the undersurface (ventricular) or the top (left atrial) surface of the leaflet. It could pierce at any point from the free margin to the main body of the leaflet equivalent to the height of the prolapsed portion of the leaflet as measured, for example, by echo imaging. The suture can be passed straight through the leaflet toward the subannular space. The suture can be passed twice through the leaflet. The suture can weave through the leaflet. The suture can form a U shape relative to the leaflet.

Figure 12A:
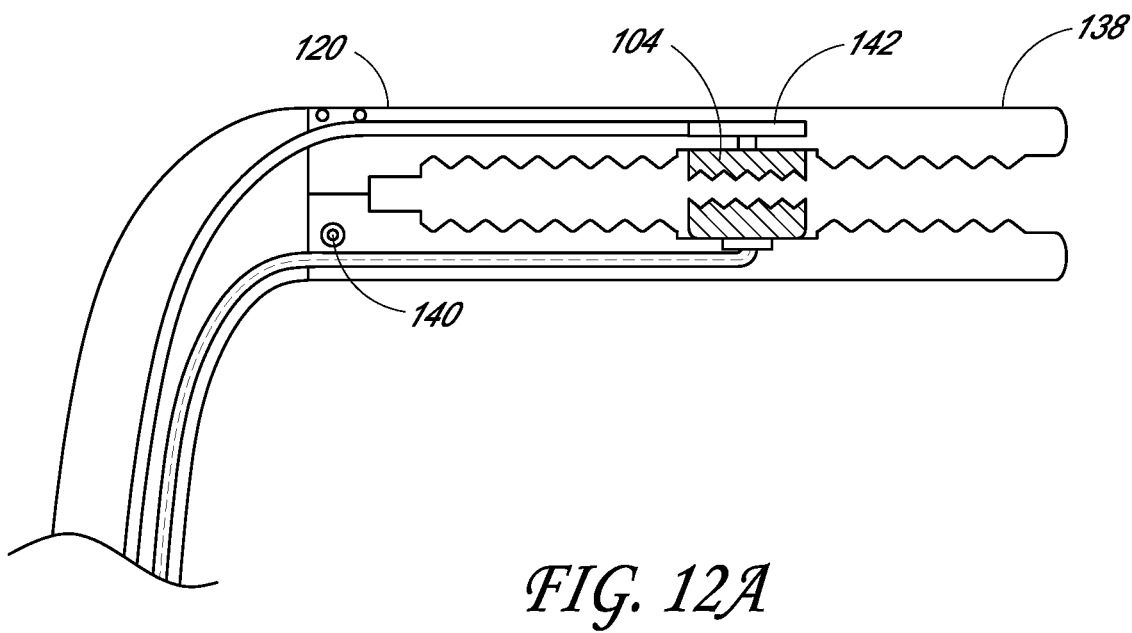
FIGS. 12A-12B show an embodiment of the leaflet capturing element and the leaflet anchor implant.
Figure 12B:
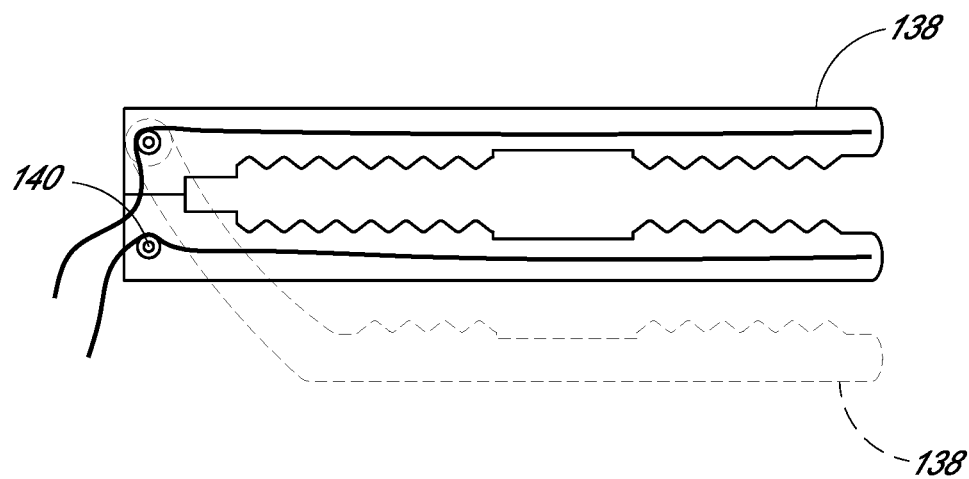

FIGS. 12A-12B show another embodiment of the leaflet capture element 120 and the leaflet anchor implant 104. FIG. 12A shows grasping arms 138 with rough grasping surfaces. FIG. 12A shows a cam mechanism 140 to open the grasping arms 138. In some methods, the leaflet can be positioned between the grasping arms 138. The cam mechanism 140 can include a rotatable cam drive. FIG. 12A also shows an implant housing 142 in the grasping arms 138. The implant housing 142 can house the leaflet anchor implant 104. In some methods, the leaflet capture element 120 can crimp the leaflet anchor implant 104 onto the leaflet. In some methods, the leaflet capture element 120 can crimp the leaflet anchor implant 104 from opposing sides. In some methods, the leaflet capture element 120 can crimp the leaflet anchor implant 104 to interlock. In some methods, the leaflet capture element 120 can release the leaflet anchor implant 104. The leaflet anchor implant 104 can include interdigitating needles. The leaflet anchor implant 104 can have pieces that couple together. FIG. 12A shows implant delivery catheters inside the grasping arms 138 with detachable implant holding attachments. The leaflet anchor implant 104 can be within the implant housing 142. FIG. 12B shows wires looping around the rotatable cam mechanisms 140 on the grasping arms 138.

Figure 13A:
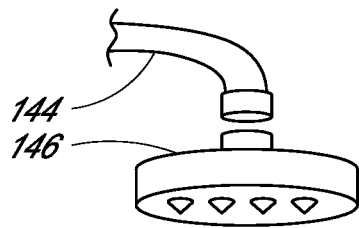
FIGS. 13A-13C show an embodiment of the leaflet anchor implant.
Figure 13B:
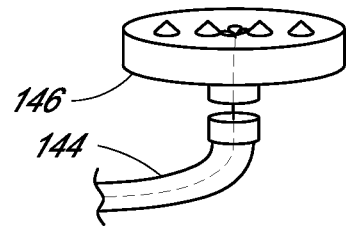
Figure 13C:
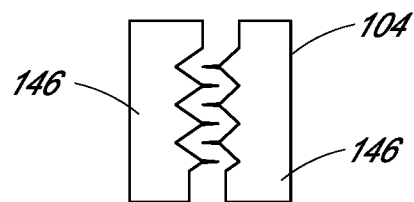

FIGS. 13A-13C show an embodiment the leaflet anchor implant 104 with interdigitating barbs or needles. The leaflet anchor implant 104 can have pieces that couple together. FIG. 13A shows an implant catheter 144 with a releasable attachment. The releasable attachment holds a disc implant 146. FIG. 13B shows another implant catheter 144 with a releasable attachment. The releasable attachment holds another disc implant 146. Each disc implant 146 has interdigitating barbs or needles. The disc implants 146 are detachable from the implant delivery catheters 144 once the two discs are engaged firmly with penetrating barbs on the discs. FIG. 13C shows the two discs 146 which form the leaflet anchor implant 104.

Figure 14:
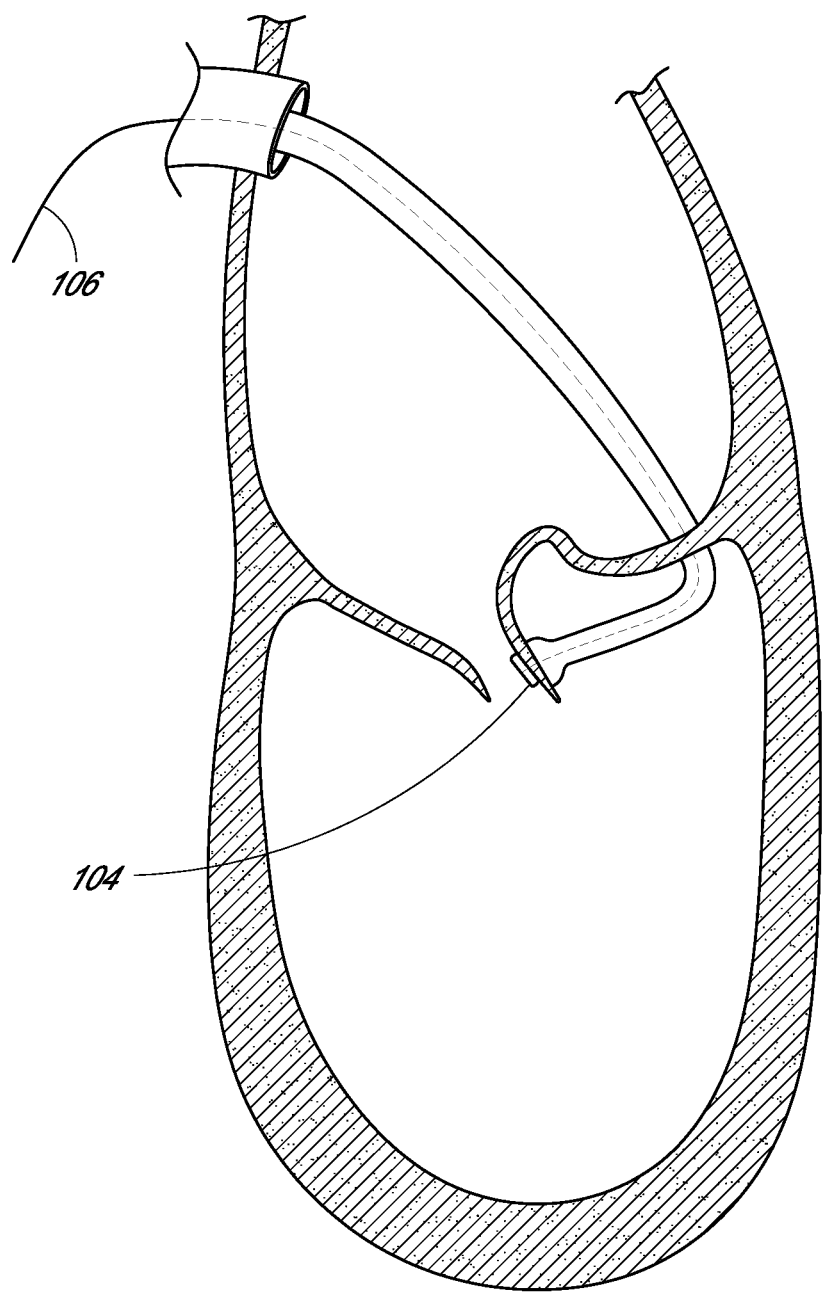
FIG. 14 shows an embodiment of the leaflet anchor implant and the tether.

FIG. 14 showing the finished leaflet implant delivery with the leaflet anchor implant 104 with the tether 106. The leaflet anchor implant 104 can be positioned on one side of the leaflet. The leaflet anchor implant 104 can be positioned on the valve side of the leaflet. The leaflet anchor implant 104 can positioned on the subannular side of the leaflet (not shown). The leaflet anchor implant 104 can crimp the leaflet therebetween two pieces. The leaflet anchor implant 104 can have any feature of any anchor.

Figure 15:
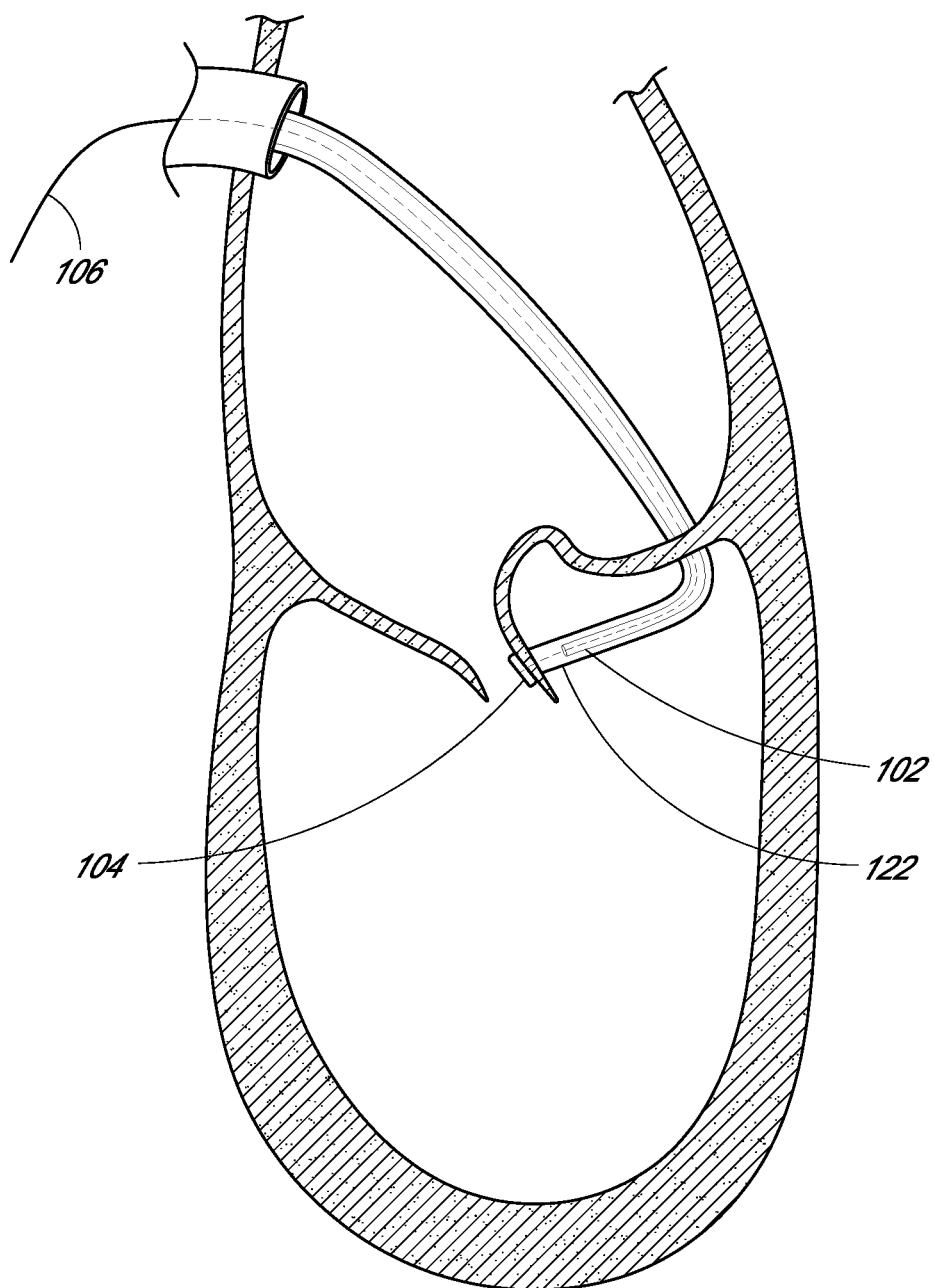
FIG. 15 shows an embodiment of a subannular implant delivery.

FIG. 15 shows the subannular implant 102 being delivered towards the leaflet. The subannular implant 102 can be delivered through the steering catheter 122. The subannular implant 102 can be delivered after the leaflet anchor implant 104 is positioned on the leaflet. The subannular implant 102 can be delivered over the tether 106. The subannular implant 102 can be compressed during delivery. The subannular implant 102 can be radially compresses to fit through the pierced hole in the annulus.

FIGS. 16A-16K shows different shapes of the subannular implant 102. The subannular implant 102 can expand to one of these shapes. The subannular implant 102 can be delivered with one of these shapes. The subannular implant 102 can include any combination of shapes. The subannular implant 102 can include a first portion having one shape and a second portion having another shape. The subannular implant 102 can be cylindrical, a prism, cuboid or any other three-dimensional shape. The subannular implant 102 can have any cross-sectional shape including round, circular, oval, triangular, rectangular, square, or any other two-dimensional shape. The subannular implant 102 can include a lumen. The subannular implant 102 can include multiple struts. The subannular implant 102 can be forked. The subannular implant 102 can be coiled. The subannular implant 102 can have one or more enlarged or flared ends. The subannular implant 102 can include a single member or a plurality of members. The subannular implant 102 can include a spring. The subannular implant 102 can include a tube. The subannular implant 102 can include a rotatable implant with a cam mechanism.

Figure 17:
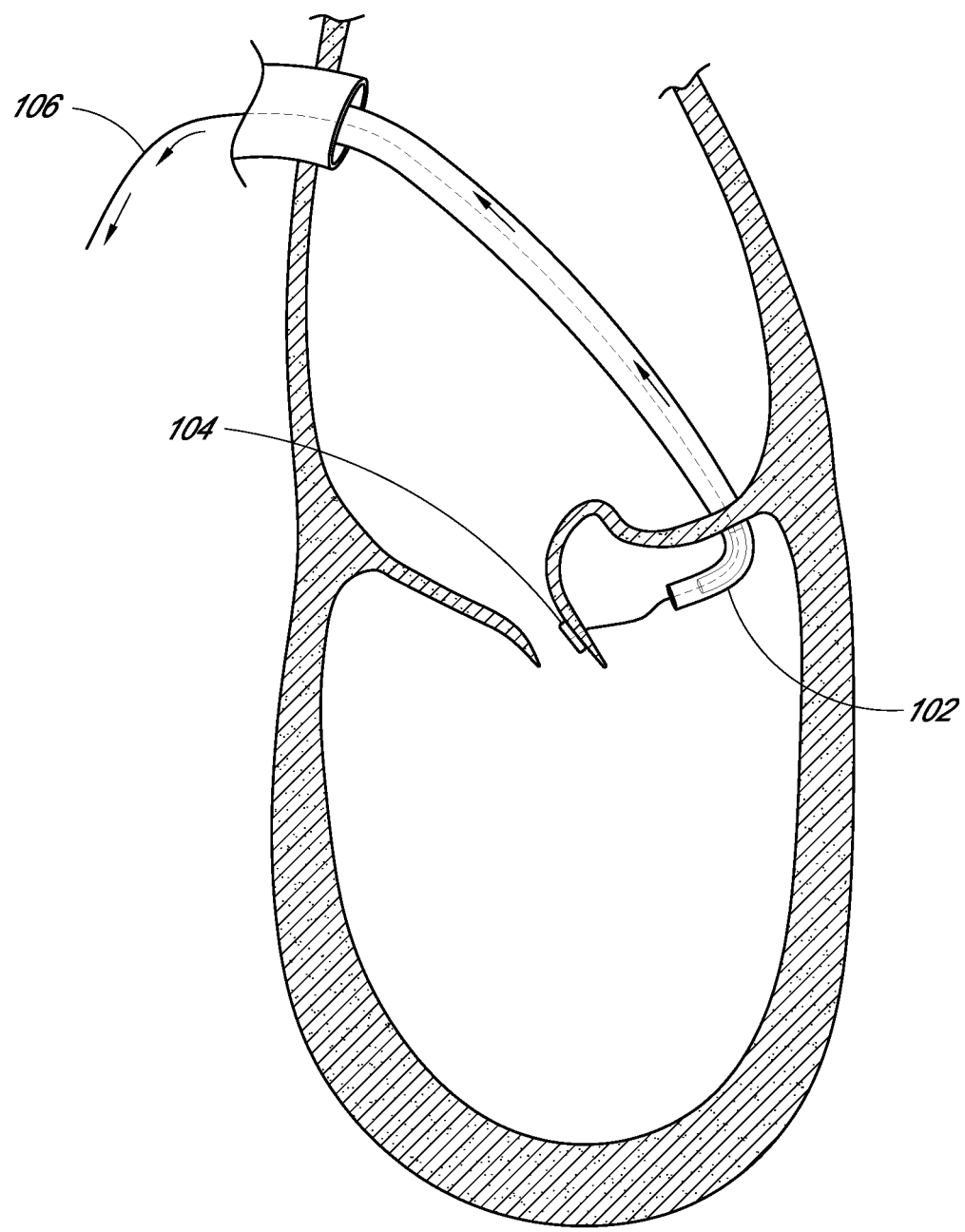
FIG. 17 shows an embodiment of a tether.

FIG. 17 shows the tether 106 being adjusted through the subannular implant 102. The tether 106 can be adjusted to reduce the degree of prolapse. The tether 106 can be adjusted by pulling the tether 106. The tether 106 can be adjusted by releasing the tether 106. In some embodiments, the tether 106 can be adjusted until the subannular implant 102 contacts the leaflet and the annulus. The subannular implant 102 can be selected to span the distance between the leaflet and the annulus. The length of the subannular implant 102 can be selected to reduce prolapse. The subannular implant 102 can be entirely positioned within the subannular space. The subannular implant 102 can abut the leaflet. The subannular implant 102 can abut the underside of the annulus.

Figure 18:
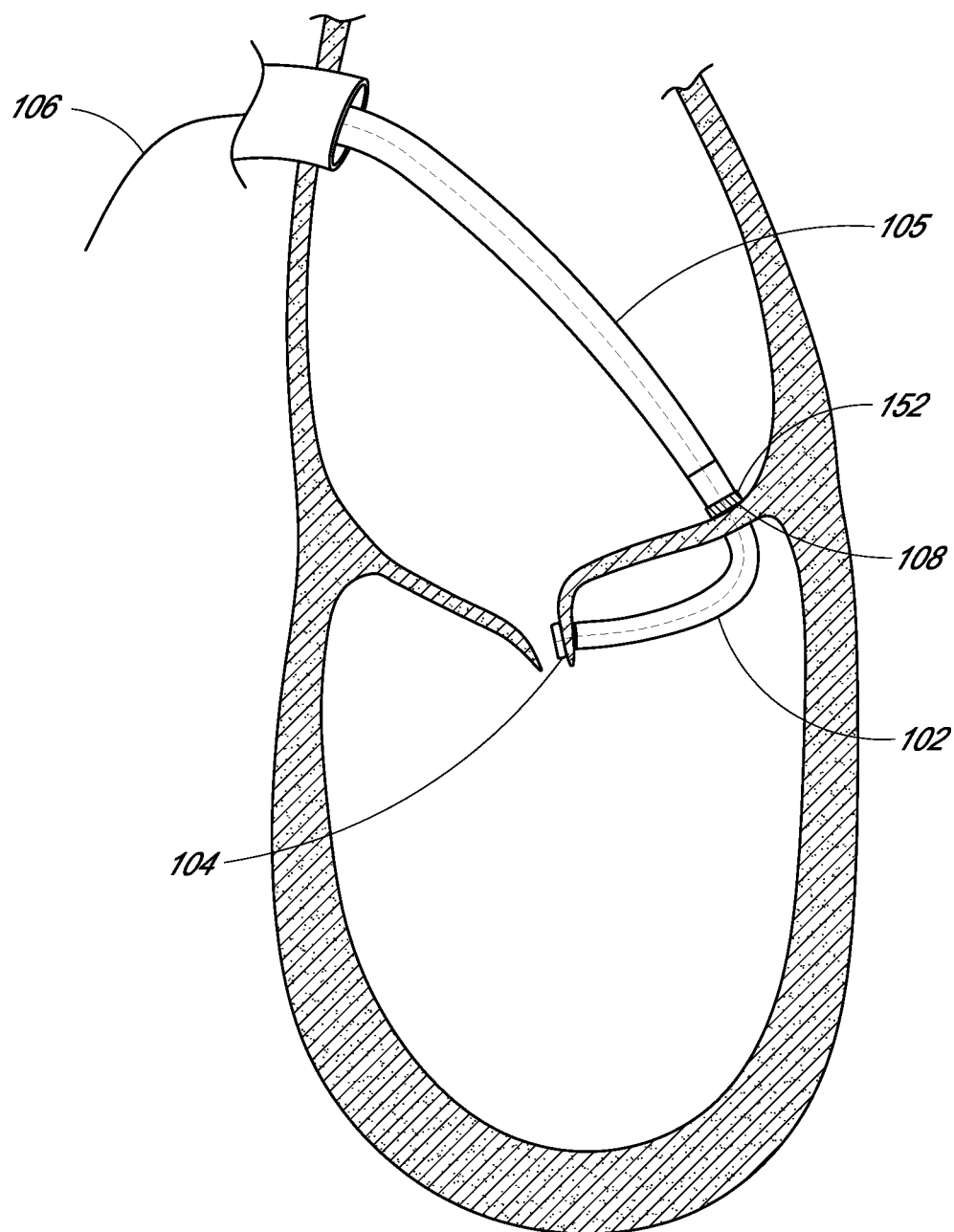
FIG. 18 shows an embodiment of a suture lock.

FIG. 18 shows complete reduction of prolapse with the leaflet anchor implant 104 and the subannular implant 102. The suture 106 can extend through the subannular implant 102. The suture 106 can extend through the annulus. FIG. 18 also shows the suture lock 108. The suture 106 can be pulled tight. The suture 106 can be pulled to positon the subannular implant 102 within the subannular space. The suture 106 can be pulled to positon the subannular implant 102 against the leaflet. The suture 106 can be pulled to positon the subannular implant 102 against the annulus. The tension of the suture 106 can be maintained. The suture lock 108 can slide along the suture 106. The suture lock 108 can abut the annulus. The suture lock 108 can be cinched with a suture lock delivery catheter 150 and a suture lock delivery component 152. The suture lock delivery component 152 can position the suture lock 108 for delivery on the annulus. The suture lock delivery catheter 150 can slide along the tether 106. The suture lock 108 can be delivered to the cinched tether 106 to retain the position of the tether 106.

Figure 19:
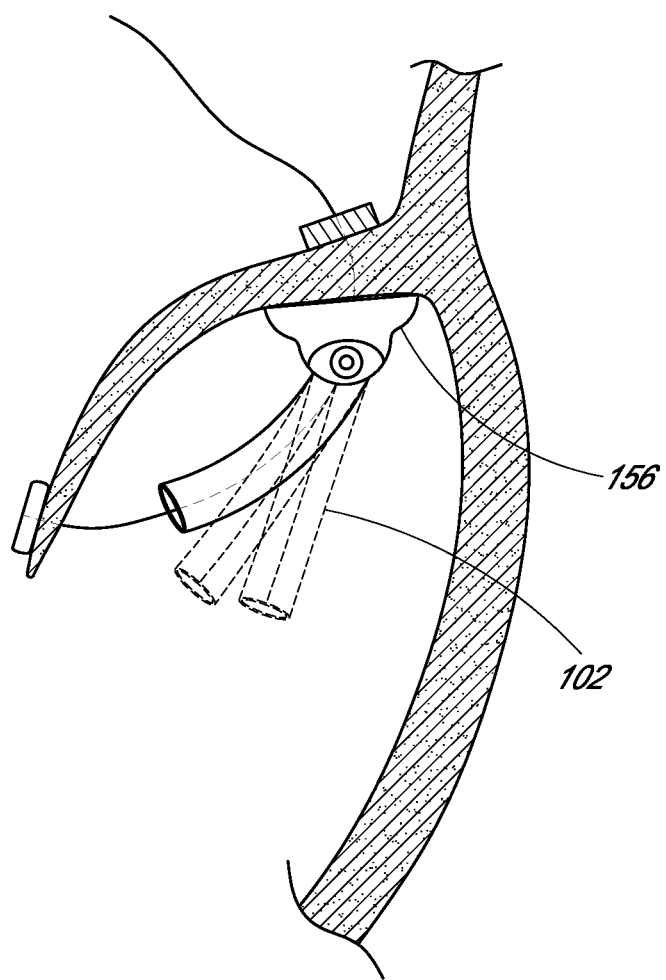
FIG. 19 shows an embodiment of a subannular implant

FIG. 19 shows a subannular rotatable cam drive 156. FIG. 19 shows the different positions of the subannular implant 102. The position of the subannular implant 102 can be actuated. The position of the subannular implant 102 can be controlled by a rotatable cam drive. The position of the subannular implant 102 can rotated relative to the annulus. The position of the subannular implant 102 can change the position of the leaflet relative to the annulus.

Figure 20A:
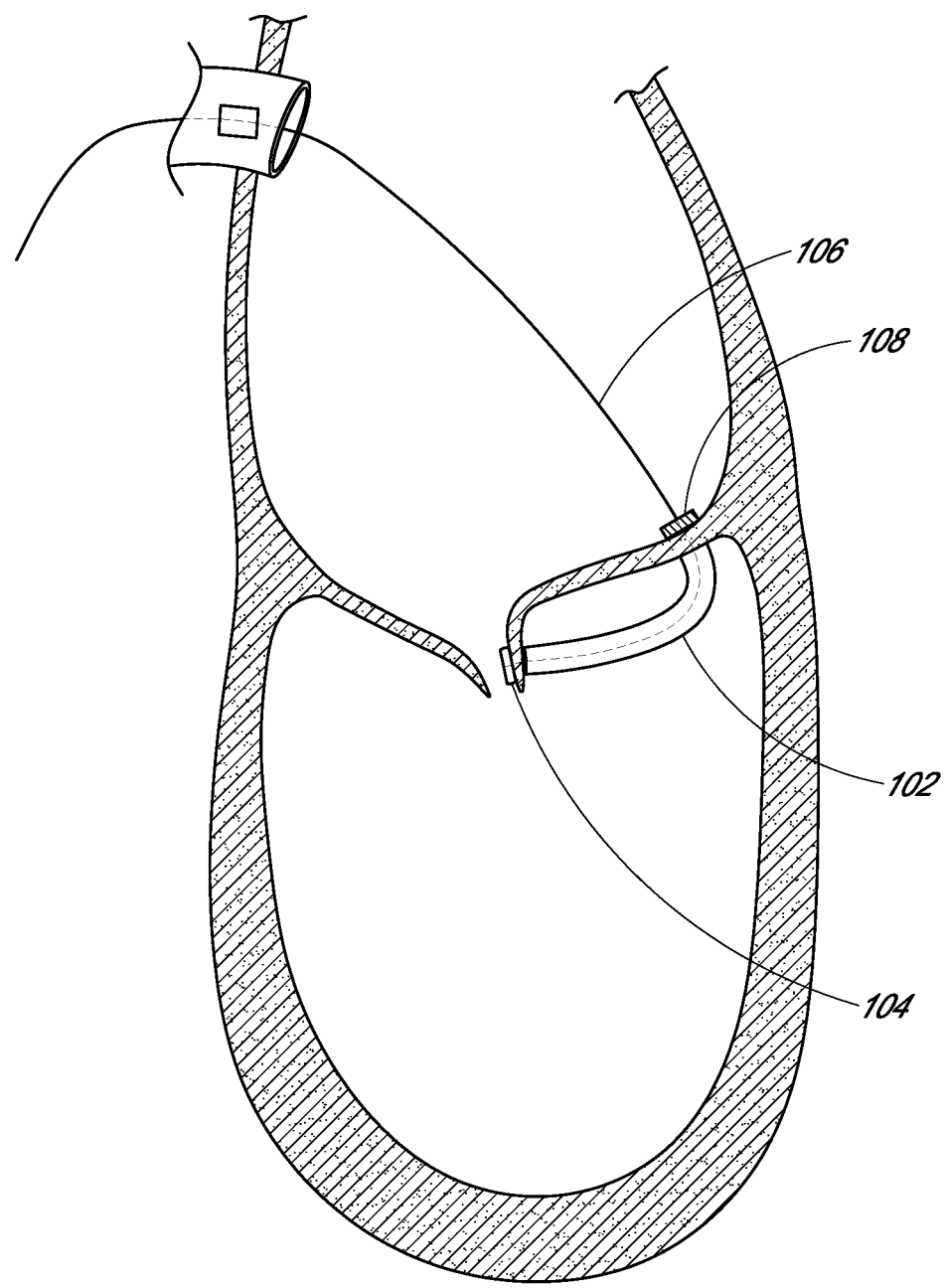
FIGS. 20A-20B show an embodiment of prolapse reduction.
Figure 20B:
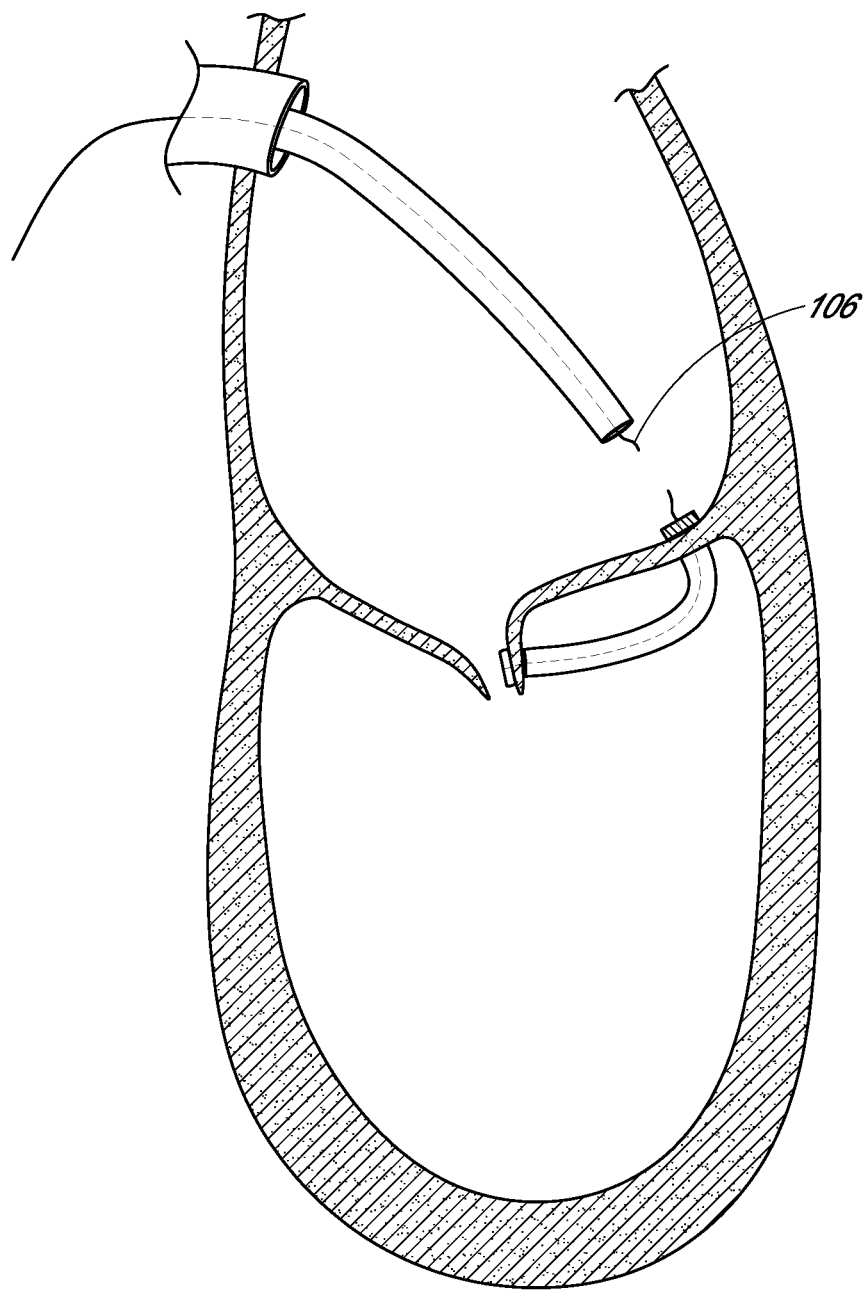

FIG. 20A shows the completed prolapse reduction with the suture lock 108 completed and the suture lock delivery system withdrawn into the guiding catheter. FIG. 20B shows the final step with the tether 106 being cut.

Figure 21:
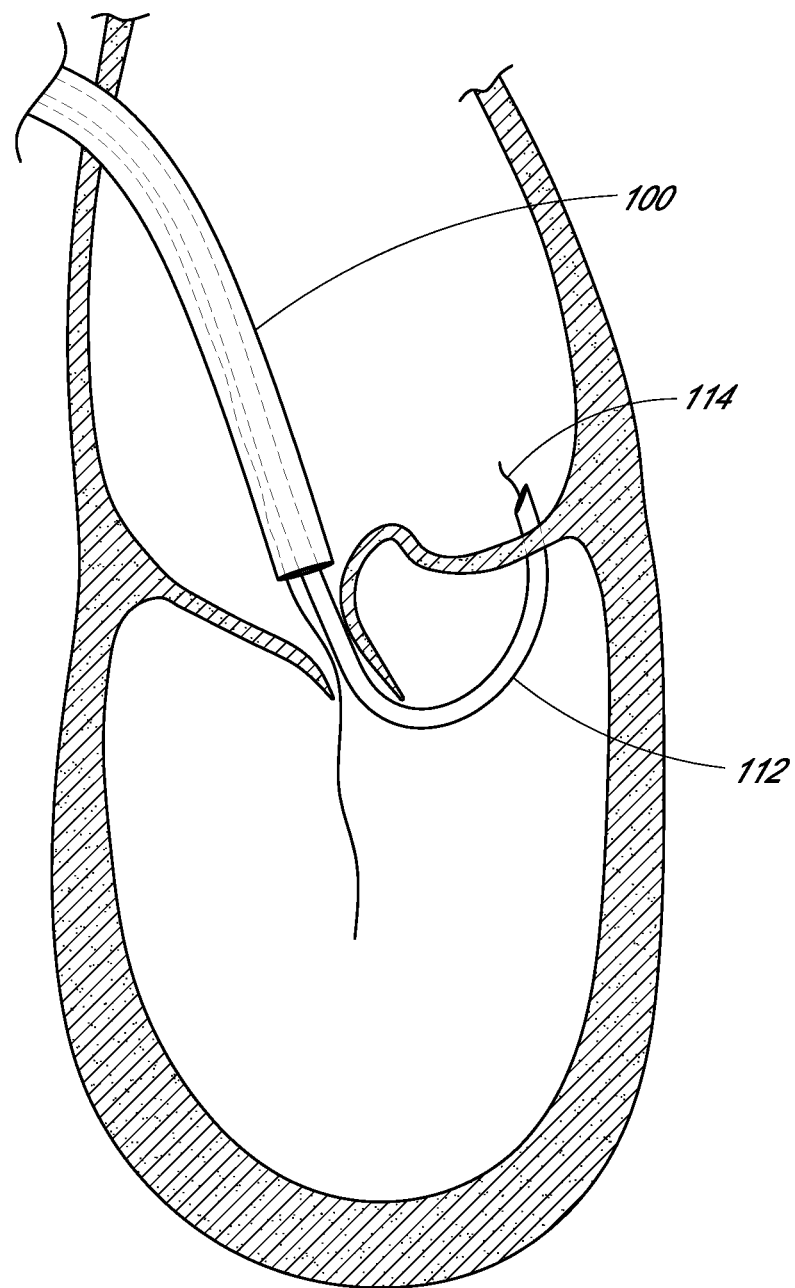
FIG. 21 shows an embodiment of penetrating the annulus.

FIG. 21 shows an alternative way of penetrating the annulus with the piercing needle 112. The guiding catheter 100 is moved through the mitral orifice from the left atrium to the left ventricle. The guiding catheter 100 can be guided by the guide wire 114. The systems and methods can be utilized by any approach. The systems and methods can pierce the annulus from the subannular space. The systems and methods can pierce the annulus from the atrium. The systems and methods can pierce the leaflet from the subannuluar space. The systems and methods can pierce the leaflet from the mitral orifice. Any method can include any combination of steps.

Figure 22:
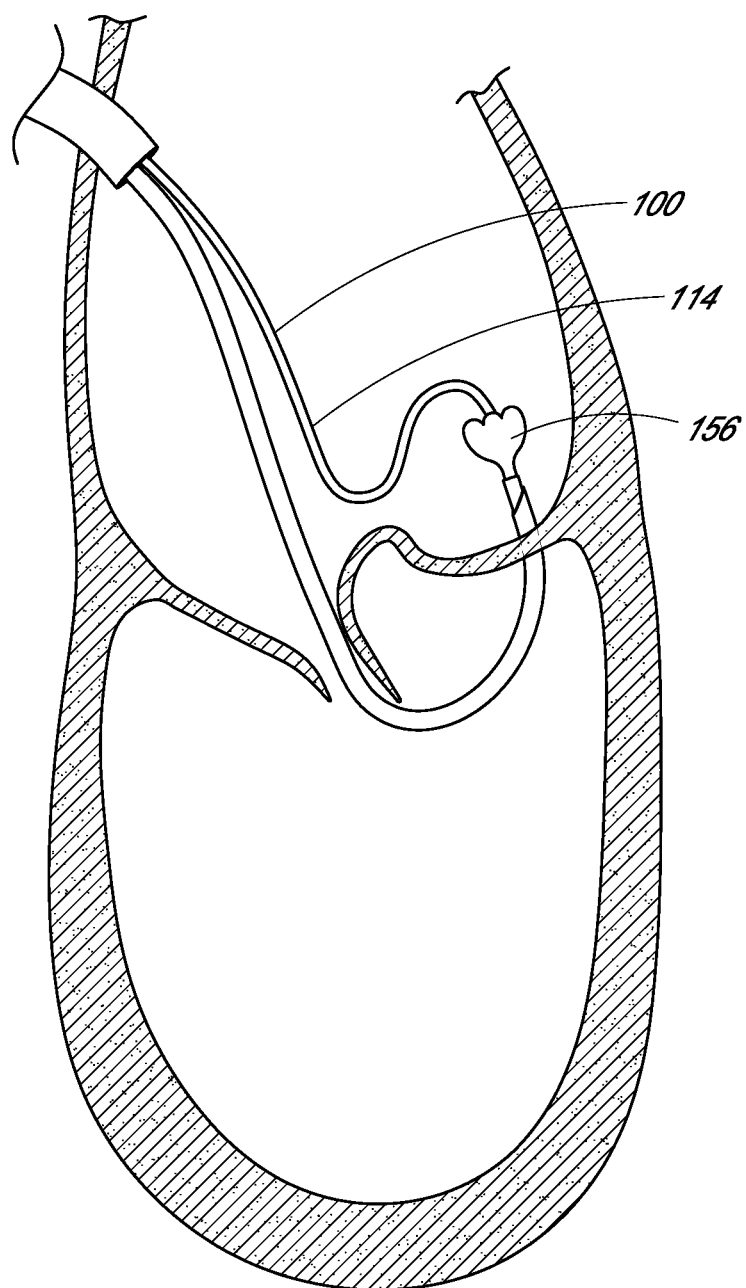
FIG. 22 shows an embodiment of a basket catheter.

FIG. 22 shows a basket catheter 156. The basket catheter 156 can be delivered in a retrograde fashion through the mitral annulus. The basket catheter 156 can catch the guide wire 114 in the left atrium, passed in an antegrade manner through the trans septal guiding catheter 100. The system can form a loop. The basket catheter 156 can extend along the leaflet and into the subannular space. The basket catheter 156 can pass through the annulus. The basket catheter 156 can capture the guide wire 114.

FIGS. 23A-23C shows various forms of the basket catheter 156. The basket catheter 156 can form a loop or lasso. The basket catheter 156 can form interlocking loops. The basket catheter 156 can have any shape to capture the guide wire 114.

Figure 24:
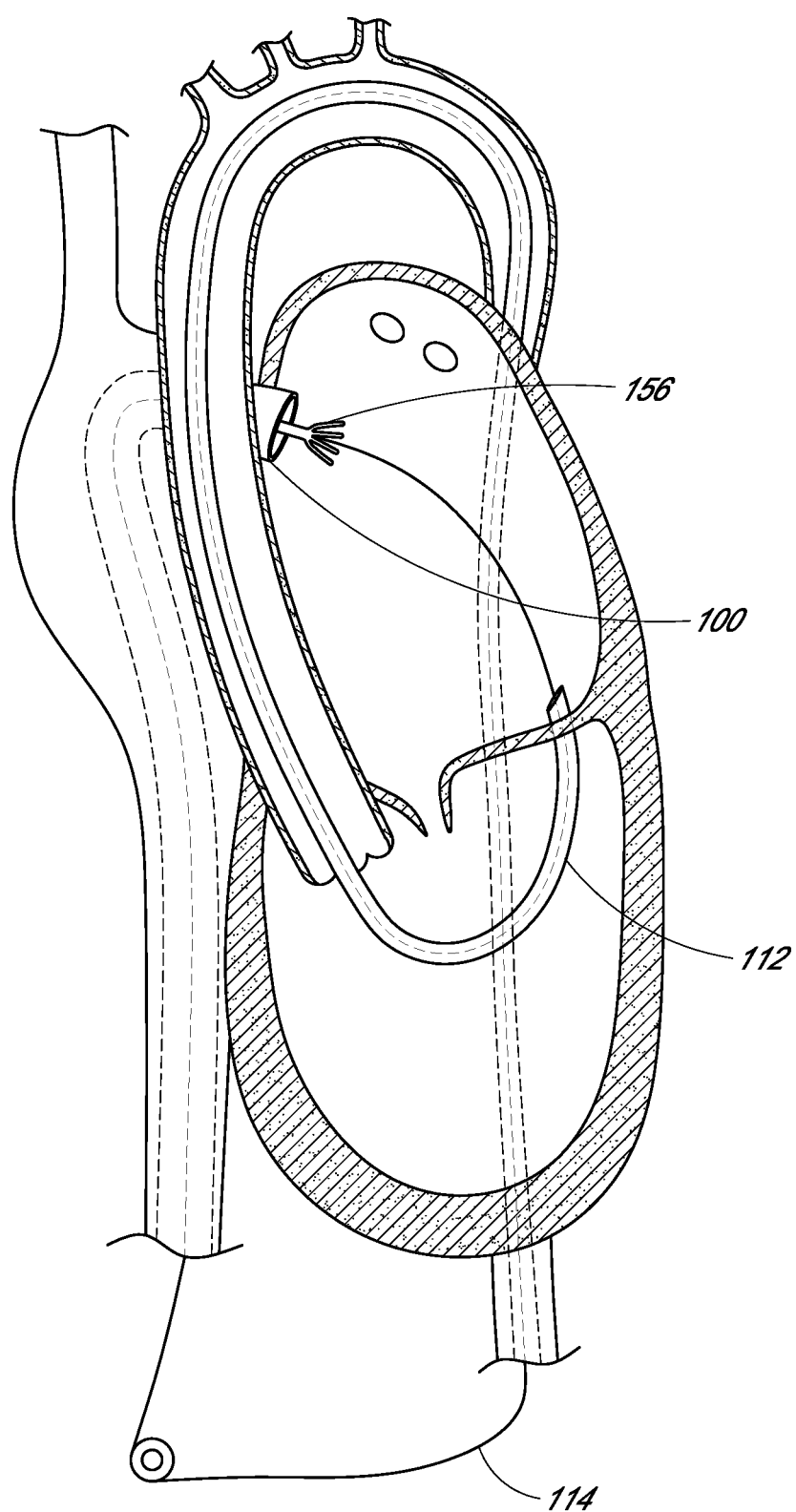
FIG. 24 shows an embodiment of a femoral artery retrograde access.

FIG. 24 shows a femoral artery retrograde access to the mitral annulus with the piercing needle 112 passed from below the mitral annulus into the left atrium. FIG. 24 shows the guide wire 114 being passed through the piercing needle 112. FIG. 24 also shows catching the guide wire 114 by the basket catheter 156 from the trans-septal guiding catheter 100 in an antegrade access via the femoral vein to form a complete wire loop through the heart chambers. The systems and methods can be utilized by any approach.

Figure 25:
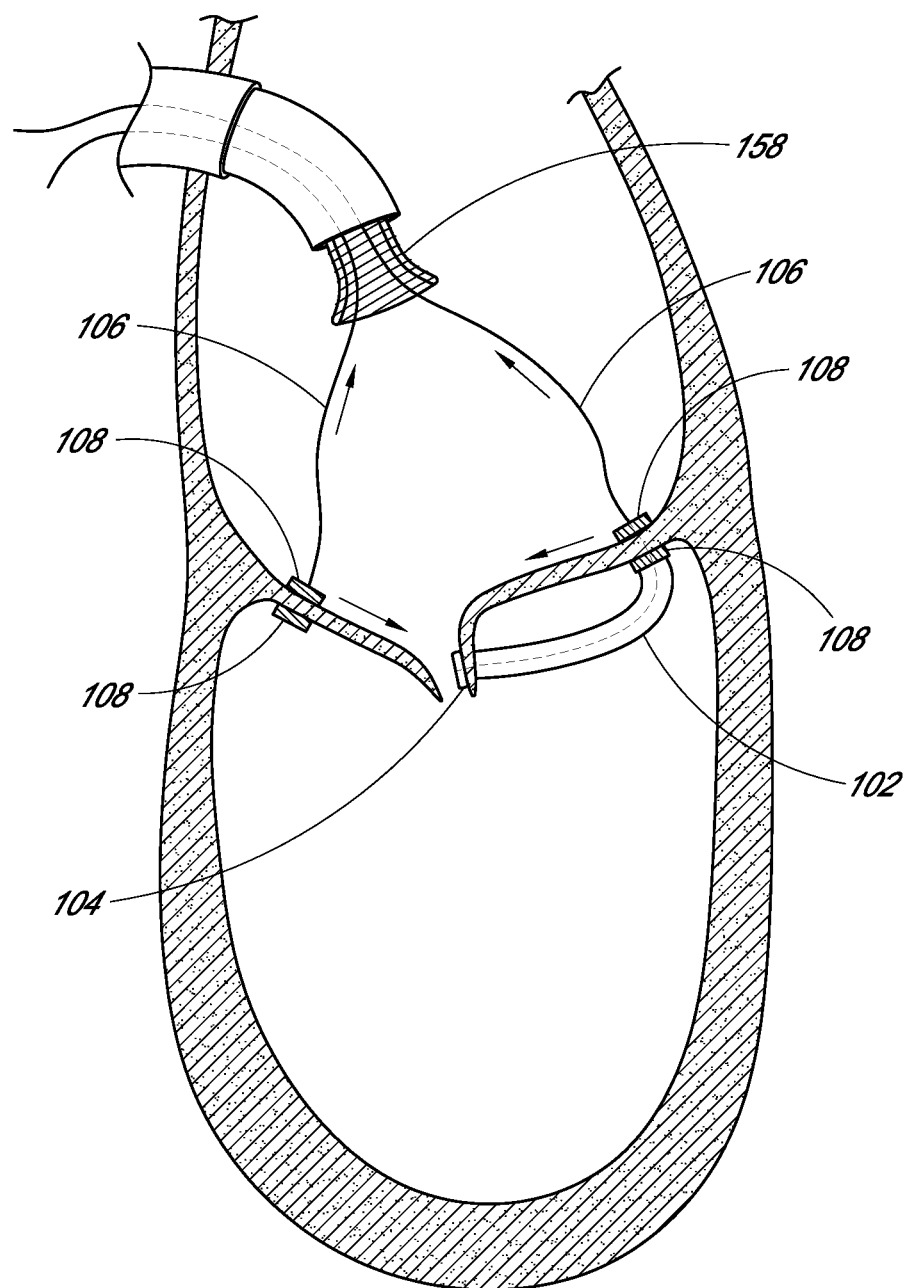
FIG. 25 shows an embodiment of anchoring systems on both leaflets.

FIG. 25 shows a completed leaflet anchor implant 104, the subannular implant 102, and a suture locks 108 on one leaflet. FIG. 25 shows only suture locks 108 on the other leaflet. The additional suture locks can be on the annulus. The additional suture locks can be on the leaflet. In some embodiments, the posterior leaflet is the prolapsing leaflet. The additional suture locks can be on the anterior leaflet. The one or more suture locks 108 can have a suture extending in the atrium. The two tethers 106 can be used to cinch the annulus. The two tethers 106 are being pulled towards each other in the left atrium to further bring the two leaflets together to enhance the coaptation. Once the coaptation enhancement is completed, the two ends of the tethers 106 are crimped together and stabilized in their final position. The stabilizing crimper 158 shown in the left atrium. The tethers 106 can be cut in the same manner as described in FIG. 20B.

Figure 26:
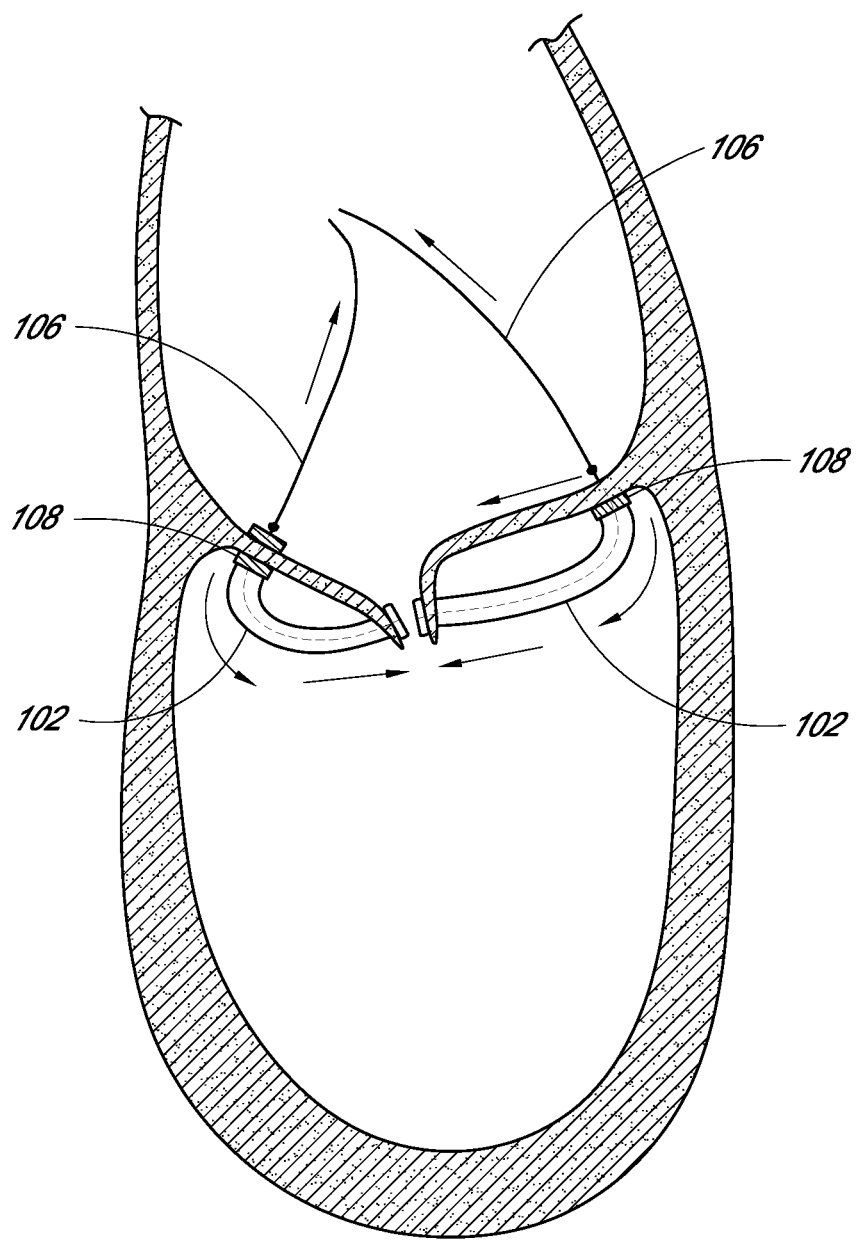
FIG. 26 shows an embodiment of anchoring systems on both leaflets.

FIG. 26 shows an alternative way of bringing the two annular tethers 106 together with two subannular implants 102. The subannular implant 102 on the anterior leaflet can be positioned and deployed in the same manner as the subannular implants 102 on the posterior leaflet. The subannular implants 102 can be deployed in a different manner using any combination of steps. Each leaflet can be coupled to a subannular implant 102. Each leaflet can be coupled to a leaflet anchor implant 104. Each leaflet can be coupled to one or more suture locks 108. The two tethers 106 can be tightened. The two tethers 106 can be brought toward each other. The two tethers 106 can be pulled proximally.

Figure 27A:
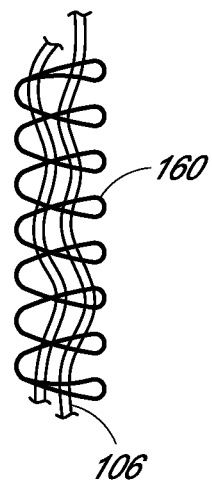
FIGS. 27A-B shows embodiments of crimping stabilizing elements.
Figure 27B:
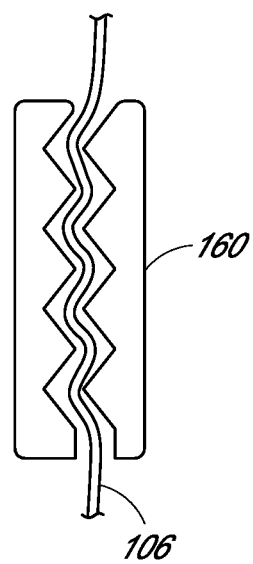

FIGS. 27A-27B show embodiments of a crimping stabilizing element 160. The crimping stabilizing element 160 can couple to two or more tethers 106. The crimping stabilizing element 160 can couple the tethers 106 together. The crimping stabilizing element 160 can maintain the tension on the sutures. FIG. 27A shows tethers 106 passed through crimping stabilizing element comprising a spring coil which can be compressed flat. FIG. 27B shows tethers 106 passed through a crimping stabilizing element with interdigitating surfaces. The crimping stabilizing element 160 can apply tension and hold one or more tethers 106.

Various other modifications, adaptations, and alternative designs are of course possible in light of the above teachings. Therefore, it should be understood at this time that the inventions may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the inventions are susceptible to various modifications, and alternative forms, specific examples thereof have been shown in the drawings and are herein described in detail. It should be understood, however, that the inventions are not to be limited to the particular forms or methods disclosed, but to the contrary, the inventions are to cover all modifications, equivalents, and alternatives falling within the spirit and scope of the various embodiments described. Any methods disclosed herein need not be performed in the order recited. The methods disclosed herein include certain actions taken by a practitioner; however, they can also include any third-party instruction of those actions, either expressly or by implication. For example, actions such as "inserting a catheter" includes "instructing the insertion of a catheter." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method of subannular anchoring, comprising:
positioning a steerable stabilizing template catheter on an annulus, wherein the steerable stabilizing template catheter comprises legs that grip the annulus;
positioning a leaflet anchor implant adjacent to a prolapsed leaflet;
positioning a subannular implant between the prolapsed leaflet and the annulus, in a subannular space;
tensioning a tether coupled to the leaflet anchor implant; and
securing the tether.

2. The method of claim 1, wherein the tether extends through the subannular implant.

3. The method of claim 1, wherein securing the tether comprises securing the tether to the annulus.

4. The method of claim 1, further comprising selecting the subannular implant from a plurality of subannular implants having different shapes.

5. The method of claim 1, further comprising selecting the subannular implant from a plurality of subannular implants having different flexibilities.

6. The method of claim 1, further comprising selecting the subannular implant from a plurality of subannular implants having different lengths.

7. The method of claim 1, wherein the subannular implant is entirely below the surface of the annulus.

8. The method of claim 1, wherein the subannular implant extends in an arc between the annulus and the prolapsed leaflet.

9. The method of claim 1, wherein the leaflet anchor implant is entirely in an mitral valve orifice.

10. The method of claim 1, wherein a lock that secures the tether is entirely in a left atrium.

11. The method of claim 1, wherein the subannular implant is less than 20 mm below the annulus.

12. The method of claim 1, further comprising piercing the annulus to access the subannular space before positioning the subannular implant.

13. The method of claim 1, further comprising positioning a leaflet capture element to grip the leaflet after passing through the annulus.

14. The method of claim 1, wherein positioning the leaflet anchor implant comprises passing the leaflet anchor implant through the leaflet from the subannular space toward an mitral valve orifice.

15. The method of claim 1, wherein tensioning the tether reduces the degree of prolapse.

16. The method of claim 1, wherein securing the tether comprises positioning a lock against the annulus.

17. A method of subannular anchoring, comprising:
piercing an annulus to access a subannular space;
piercing a leaflet from the subannular space toward an mitral valve orifice;
passing a leaflet anchor implant through the leaflet from the subannular space toward the mitral valve orifice, the leaflet anchor implant coupled to a tether;
positioning a subannular implant between the leaflet and the annulus, in a subannular space, wherein the tether passes through a lumen of the subannular implant;

passing the tether through the annulus;
tensioning the tether; and
securing the tether by positioning a lock against the annulus.

18. The method of claim 17, wherein the subannular implant is less than 20 mm below the annulus.

19. The method of claim 17, wherein the leaflet is anchored to the annulus to reduce prolapse by pulling a prolapsed free margin of the leaflet toward an undersurface of the annulus.

* * * * *